United States Patent [19]
Tao et al.

[11] Patent Number: 5,976,872
[45] Date of Patent: Nov. 2, 1999

[54] BRAIN TRANSCRIPTION FACTORS, NUCLEIC ACIDS ENCODING SAME AND USES THEREOF

[75] Inventors: Wufan Tao, Branford, Conn.; Eseng Lai, New York, N.Y.

[73] Assignee: Sloan-Kettering Institute for Cancer Research, New York, N.Y.

[21] Appl. No.: 08/331,644

[22] PCT Filed: Apr. 30, 1993

[86] PCT No.: PCT/US93/04102

§ 371 Date: Feb. 21, 1995

§ 102(e) Date: Feb. 21, 1995

[87] PCT Pub. No.: WO93/23430

PCT Pub. Date: Nov. 25, 1993

Related U.S. Application Data

[63] Continuation-in-part of application No. 07/882,292, May 13, 1992, Pat. No. 5,324,638.

[51] Int. Cl.$^6$ ............................ C12N 15/52; C12N 15/62; C07H 17/00
[52] U.S. Cl. ...................... 435/320.1; 536/23.4; 536/23.2
[58] Field of Search ........................ 435/320.1; 536/23.1, 536/23.5, 23.4, 232; 530/350

[56] References Cited

U.S. PATENT DOCUMENTS 5,324,638  6/1994  Tao et al. ................................ 435/69.1

OTHER PUBLICATIONS

Costa, R. et al., Multiple hepatocyte–Enriched Nuclear Factors Function in the Regulation of Transthyretin and α1–Antitrypsin Genes, Molecular and Cellular Biology (1989) vol. 9: 1415–1425.

Courey, A. J. and Tjian, R., Analysis of Sp1 In Vivo Revesals Multiple Transcriptional Domains, Including a Novel Glutamine–Rich Activation Motif, Cell (1988) vol. 55: 887–898.

Davis, C., A. et al., Expression of the Homeo Box–Containing Gene En–2 Delineates a Specific Region of the Developing Mouse Brain, Genes & Development (1988) vol. 2: 361–371.

Davis, C. and Joyner, A. L., Expression Patterns of the Homeo Box–Containing Genes En–1 and En–2 and the Proto–Oncogene int–1 Diverge During Mouse Development, Genes & Development (1988) vol. 2: 1736–1744.

He, X., et al., Expression of a Large Family of POU–Domain Regulatory Genes in Mammalian Brain Development, Nature (1989) vol. 340: 35–42.

He, X. and Rosenfeld, M. G., Mechanisms of Complex Transcriptional Regulation: Implications for Brain Development, Neuron (1991) vol. 7: 183–196.

Kessel, M. and Gruss, P., Murine Development Control Genes, Science (1990) vol. 249: 374–379.

Lai, E., et al., HNF–3A, A Hepatocyte–Enriched Transcription Factor of Novel Structure is Regulated Transcriptionally, Genes & Development (1990) vol. 4: 1427–1436.

Li, C. et al., Cloning of a Cellular Factor, Interleukin Binding Factor, That Binds to NFAT–like Motifs in the Human Immunodeficiency Virus Long Terminal Repeat, Proc. Natl. Acad. Sci. USA (1991) vol. 88: 7739–7743.

Mermod, N., et al., The Proline–Rich Transcriptional Activator of CTF/NF–1 is Distinct From the Replication and DNA Binding Domain, Cell (1989) vol. 58: 741–753.

Mori, K., et al., Telencephalon–Specific Antigen Indetified by Monoclonal Antibody, Proc. Natl. Acad. Sci. USA (1987) vol. 84: 3921–3925.

Price, M., et al., A Mouse Gene Related to Distal–Less Shows a Restricted Expression in the Developing Forebrain, Nature (1991) vol. 351: 748–750.

Weigel, D. and Jackle, H., The Fork Head Domain: A Novel DNA Binding Motif of Eucaryotic Transcription Factors. Cell (1990) vol. 63: 455–456.

Wilkinson, D.G., et al., Segmental Expression of Hox–2 Homoeobox–Containing Genes in the Developing Mouse Hindbrain, Nature (1989) vol. 341: 405–409.

Clevidence et al. 1993 PNAS 90:3948–3952.

Pani et al. 1992 Mol. Cell Biol 12:3723–3732.

Murphy et al 1994 Genomics 21:551–557.

Pierrou et al 1994 EMBOJ 13:5002–5012.

Pai et al 1991 Genes Devel 5: 416–427.

Pai et al 1993 PNAS 90:10421–10423.

Li et al 1993 PNAS 90:4490–4494.

Hatini et al 1994 J Neurobiol 25:1293–1309.

*Primary Examiner*—Robert A. Wax
*Assistant Examiner*—K. Cochrane Carlson
*Attorney, Agent, or Firm*—John P. White; Cooper & Dunham LLP

[57] ABSTRACT

This invention provides an isolated, animal nucleic acid molecule encoding the Brain Factor-1, Brain Factor-2 and Brain Factor-3. This invention also provides expression vectors containing these nucleic acid molecules, host vector systems containing the vectors and a method of producing the Brain factor comprising growing the host vector system under suitable conditions. This invention also provides a DNA vector which comprises the 5' nontranscribed region of the Brain Factor-1 gene, 3' nontranscribed region of the Brain Factor-1 gene and a gene of interest, linked operably.

12 Claims, 22 Drawing Sheets

FIG. 1A

```
GGGGGCCGCTTCCGGGACGGCCCCGCGGGCGCCGGCTGCCCCCCTTCGGGCTCTCCCCGGCTGCCGCTGCTGTGACT           76
GCTGCGGGCGCGAGGAGGAGGAGGGAGGCCGAGGGGAGGGGGCGAACGGAGCCGAGGGGCTGCTGCACCCCGGGC          154
GACGGGTTGCTTCTGCCTTCTAGCTTCTCTCTCTCTCTCTTCTCTCTCTCTCTCTCTCTCTCTCTCTCTCTCTCTC          232
TCTCTCTCTAATTCTTGAGGGGTGGTTGCAGCTTTTGCTACATGCGTGCCAGCCTTGCCAGCCTGCGGTCAACTGCG          310
CTGCCGGAGCGCTCAGTGCCGTGCCAGTCCCTGCCCCGCTGCCCCCCACTCCGAACCCGCCGGTCGCTGCCG          388
CGCTGCTGCTCGGTCCTGCGCCCCGCCCGTCCTGCGCCCCCCGACGCTGGGTGATGCTGGACATGGGAGATAGGAAA          466
                                                   M   L   D   M   G   D   R   K     8

GAGGTGAAAATGATTCCCAAGTCCTCGTTCAGCATCAACAGCCTGGTCCCTGAGGCCGTCCAGAACGACAACCACCAC          544
 E   V   K   M   I   P   K   S   S   F   S   I   N   S   L   V   P   E   A   V   Q   N   D   N   H   H    34

GCGAGCCACGGTCACCACACAGCCACCACCATCATCACCATCATCACCACCCCGCCCCCGCCC          622
 A   S   H   G   H   H   N   S   H   H   P   Q   H   H   H   H   H   H   H   P   P   P   P    60

GCGCCTCAGCCGCCACCCCAGCCCCCAGCAGCAGCCCCGCCTTCTGCTCCCCAGCCGCCAGGCGCCGGC          700
 A   P   Q   P   P   P   P   Q   Q   Q   Q   Q   P   P   A   P   Q   P   P   Q   A   R   G    86

GCCCCAGCAGCCGACGACGATGACAAGGGCCCCCAGCCACAGCCGCTTCTCCCGCCCTCCGCTGACGGGCCAAGGCT          778
 A   P   A   A   D   D   D   K   G   P   Q   P   L   L   P   P   S   A   A   L   D   G   A   K   A   112

GACGCCACTTGGAGCCAAAGGCGAGCCGGGCGAGCTGGCCGGGCCCGCTGAGCTGGCCCCCGTCGGCCCTGACGAAGGAGAAG          856
 D   A   L   G   A   K   G   E   P   G   G   G   P   A   E   L   A   P   V   G   P   D   E   K   E   K   138

GGCGCGGGCGCTGGGGGCGCTGGGGGAGGAGAAGAAGGGGCCGAGGACGGGCAAGGACGGGGAAGGAGGGGAC          934
 G   A   G   G   E   E   K   K   G   A   G   E   G   G   G   K   D   G   E   G   G   K   E   G   D   164
```

FIG. 1B

```
AAGAAGAACGGCAAGTACGAGAAGCCGCCGTTCAGCTACAACGCGCTCATCATGATGGCCATCAGGCAGAGTCCCGAG   1012
 K  K  N  G  K  Y  E  K  P  F  S  Y  N  A  L  I  M  M  A  I  R  Q  S  P  E        190

AAGCGGCTGACGCTCAACGGCATCTACGAGTTCATCATGAAGAACTTCCCTTACTACCGGGAGAACAAGCAGGGCTGG   1090
 K  R  L  T  L  N  G  I  Y  E  F  L  M  K  N  F  P  Y  Y  R  E  N  K  Q  G  W     216

CAGAACTCCATCCGCCACAACCTGTCCCTCAACAAGTGCTTCGTGAAGTACCGCCACTACGACGACCCGGGCAAG      1168
 Q  N  S  I  R  H  N  L  S  L  N  K  C  F  V  K  Y  R  H  Y  D  D  P  G  K        242

GGCAACTACTGGATGCTGGACCCGTCGGACGACGTGTTCATCGGGGGCACCGGAAGTCGCGGCCGCTCC            1246
 G  N  Y  W  M  L  D  P  S  D  D  V  F  I  G  G  T  T  G  K  L  R  R  R  S        268

ACCACGTCTCGGGCAAGCTAGCCTTTAAGCGGGGCGCCCGTCTCACCTCCACCGGCCTCACCTTCATGGACCGCGCC    1324
 T  T  S  R  A  K  L  A  F  K  R  G  A  R  L  T  S  T  G  L  T  F  M  D  R  A     294

GGCTCCCTCTACTGGCCCATGTCGCCCTTCCTGTCCCTGCACCACCCTCGGCCAGCAGCACTTTGAGTTACAACGGG    1402
 G  S  L  Y  W  P  M  S  P  F  L  S  L  H  H  P  R  A  S  S  T  L  S  Y  N  G     320

ACCACGTCGGCCTACCCGAGCCACCCCATGCCCTACAGCTCCGTGTTGACTCAAAACTCGCTGGGCAACAACCACTCC   1480
 T  T  S  A  Y  P  S  H  P  M  P  Y  S  S  V  L  T  Q  N  S  L  G  N  N  H  S     346

TTCTCCACCGCCAACGGGCTGAGCGTGGACCGGCTGGTCAACGGGGAGATCCCGTACGCCACCACCTCACGGCC       1558
 F  S  T  A  N  G  L  S  V  D  R  L  V  N  G  E  I  P  Y  A  T  H  H  L  T  A     372
```

FIG. 1C

```
                                                                              1636
GCTGGCGCTCGCCGGCCTCCCGTGCCCTGCGGTCCGCTGCTCCTCAACCCCTGCTCCGTC
 A  A  L  A  A  S  V  P  C  G  L  S  V  P  C  S  G  T  Y  S  L  N  P  C  S  V   398

1714
AACCTGCTCGCGGGCCAGACCAGTTACTTTTTCCCCCACGTCCCCACCTCAATGACTTCGCAGACCAGCACGTCC
 N  L  L  A  G  Q  T  S  Y  F  F  P  H  V  P  H  P  S  M  T  S  Q  T  S  T  S   424

1792
ATGAGCCGGGCCGCCGGTCCTCCTCTACGTCGCCGCAGGCCCCCTCGACCCTGCCCTGTGAGTCTTTAAGACCCTCT
 M  S  R  A  A  S  S  T  S  P  Q  A  P  S  T  L  P  C  E  S  L  R  P  S       450

1870
TTGCCAAGTTTTACGACAGGACTGTCCGGGGACTGTCTGATTATTCACACATCAAAATCAGGGGTCTTCTTCCAAC
 L  P  S  F  F  T  T  G  L  S  G  G  L  S  D  Y  F  T  H  Q  N  Q  G  S  S  N   476

1948
CCTTTAATACATTAACATCCCGGGACCAGACTGTAAGTGAACGTTTACACACATTGCATTGTAAATGATAATTAA
 P  L  I  H  *                                                                 480

AAATAAGTCCAGGTATTTTTTATTAAGCCCCTTCCCCCCATTTCTGTACGTTTGTTGTTCAGTCTTTAGGGTTGTTTACTA  2026
TTCTAACACGGTGTGGAGTGTCAGCAGCGAGGTGCAATGTGGGAGAATACATTGTAGAATATAAGGTTTGGACGTCAA     2104
ATTATAGTAGAAATGTGTATCTAAATAGTGACTGTTGCCATTCATTCAAACCTGACAAGTCTATCTCTAAAGGCTG      2182
CCAGATTTCCATGTGCAGTATTATAAGTTATCATGGATCTATCTGGTGGACGCAGGCCTTGAAGAACAACCTAAAT      2260
TATGAAGAGAGTTTAAATGTTAAACTGTTTTCCTTTCTTTGTTTTCCTTTGTTATTGTAGTAAGGTGCCCAAGAAATTATATTG 2338
GCCATTTATTGTTTGTCCTTTAGAACTGTTTTTGTTTTCCTTTTCTTTGTTTACTTTTAGACCAAAGATTGGATTCT       2416
AGCAAATGCACTTGGTATACTAAGTATTAAACAAGCAAACAAAACAAAAAAGGAAGGTTGTTTAGTTTGGCAA           2494
CACTGCCCATTCAATGAATCCGAAGGACAAATTGCCTTCAGTTTGTGTATATTTCGATGTATG                   2572
TGGTCACTAACAGTCACTTTATTTTCTAAATGTAGTGAAATGTTAATACCTATTGTACTTATAGTAAACCTTG          2650
CAAATGTAACCTGGTCGCAAATGCCGCATCAATTGAGTGATTGTTAATCTTTAAAATTCTTGATTGT                2728
GATACTGTGGTCATATGCCCTGTTGTCACTTACACAAAAATGTTTACTATGAACACAGAAATAAAATAGGCTAA         2806
ATTCATATATAAAAAAAAAAAAA                                                           2832
```

FIG. 5E  FIG. 5F  FIG. 5G  FIG. 5H
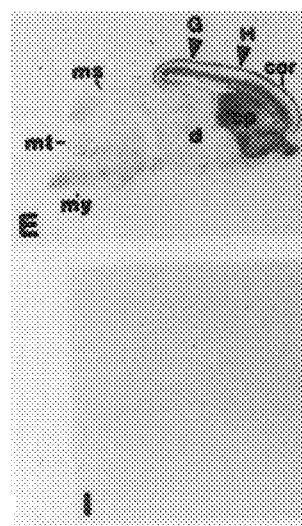
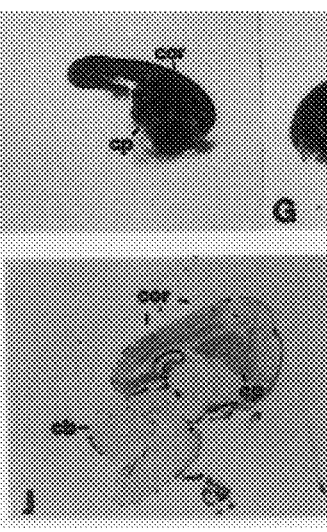
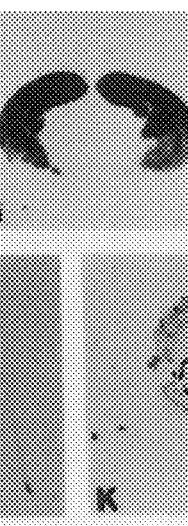
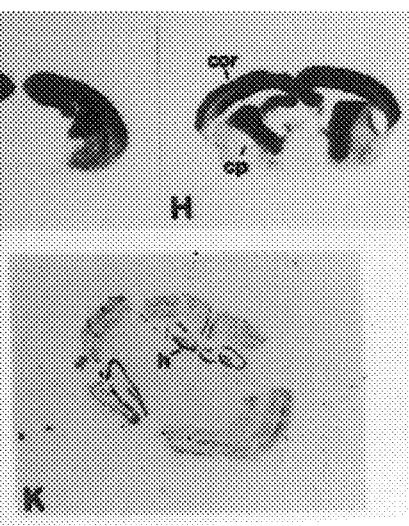
FIG. 5I  FIG. 5J  FIG. 5K

FIG. 10A

BF-2 cDNA

DNA sequence  1860 b.p.  GGCCTTGCCGAG ... AAAAAAAAAAAA  linear

```
          10         20         30         40         50         60
          |          |          |          |          |          |
  1 GGCCTTGCCG AGCTCCGTTT CTAGATTCTC ACTCCTCCCG CGCCCTTCTG GGCGCCCGAC   60
 61 ACCGACTGGC CGCCAGGGT CCAGCCACCC CCTCCTGGAC TAACCGGGCT AAAGGGACCA  120
121 CAGTGGAAAA GGTCAAGTCT AGAGCGCCCG CCACCCGGTG CCCGCCGAGC CGGGGAGCGC  180
181 AAACACCTCG CACAGCCCTG CTCGCCAAGT AGCGGGAGCGG AGGGCCCCCA GCCACCTCCT  240
241 GCAGCCGCGC GTCGCAGAGT GGCGTCCTCG CTCCGGGTCC GCCCCTCCGG GATCGGCCTG  300
301 GGGAGGCCAG GGAGCCGGA GCCCGGTGCC CCTATGTGCC GCCGCCCAC CGCGCCCGCC  360
361 CAGCTATGAC CCTGAGCACG GAGATGTCCG ATGCCCTCCG GAGGAGGAG CCTCGCGGAG GAGACAGACA  420
421 TCGACGTGGT GGGGAGGC GAGGACGACG AGGAGGAGGA GGACGATGAC GACGAGGGCG  480
481 GCGGCGGCCG CGGCGGCGGG GGGTCCCCGT TGCCGAGCTC GGCCCAGCGG CGGAGGCGCT  540
541 CTTACGCCCG GGAGGTCGAT CTCGAGGACC TGGAGGAGGA GGACGACGAT GACCTGCTGC  600
601 TGGCCCCCCG GCCCGCCGCG TCCCCCGCG CTCCGGGTCC TGCGCCCGCC CCGGGGACGG  660
661 GGTCGGGGCG CTGCAGCGGC GCCGGAGCGG GAGGCGGCGC GGGAGGTGGT ACGGGCGCGG  720
721 GCACGGGGCG GGGCGCTAAG AATCCGCTGG TGAAGCCGCC CTACTCGTAC ATCGCGCTCA  780
781 TCACCATGGC CATCCTGCAG AGCCCCAAGA AGCGCCTGAC GCTCAGCGAG ATCTGCGAGT  840
841 TCATCAGCAG CCGCTTCCCT TACTACCGGG AGAAGTTCCC CGCTTGGCAG AACAGCATCC  900
901 GTCACAACCT GTCGCTCAAC GACTGCTTCG TCAAGATCCC GCGCGAACCG GGCAACCCGG  960
961 GCAAGGGCAA CTACTGGACG CTCGACCCCG AGTCCGGCAGA TATGTTCGAC AACGGCAGCT 1020
```

FIG. 10B

```
1021  TCCTGCGGCG  CCGCAAGCGC  TTCAAGCGCC  AGCCGCTACT  CGATCCCGCG  CTGGGACTC  1080
1081  TGCACCAAGG  GACAGCGCTG  TCCAGTGTGG  AGAACTTTAC  TGCTAGGATT  TCCAATTGTT  1140
1141  AGGAACGTCG  TTAGCGCGCG  GGAGAGCGAA  GGTAGGACTC  CCGGCTTCTT  TCTCCGGATG  1200
1201  GGGGGTTGG   TTTCGTTCGC  CCCTCCCGGT  CCTCGGAGAC  CCCGCGCCCC  CCGTTTTCGC  1260
1261  CGCTTCGGAT  TCTTGGACCA  GACTGTGTTG  GCCGACAGCT  GGGGCGCCCGC  GCAGTTTAGC  1320
1321  TCAGAGGGTC  CATCTATTTA  TGCAAAATCG  CCCTATGCTG  CAACCCTGAC  TTGGGGTGGG  1380
1381  AAGGAGGGA   GTCGCTCTGT  CTTGGCACTA  GGAATTTCCT  TGACTTTTGA  CAAATTGAGA  1440
1441  AAAAACAAAA  CAAAACAAGC  AAAATCATCA  AACTAAGCC   CTTTTTGAGG  TGTAGAGATT  1500
1501  CACAGTCCA   GCGTTTTAAA  AAATCAGTAA  TGTTTAAATG  CAGCTTATAG  AAAACCAGTA  1560
1561  AAAGTCTCCA  AGAAATGCCT  CTACTTGTTC  ACACTTGTTT  GGTAGACTTT  TTTCATGGAA  1620
1621  AGAAAAAAAA  TTAACATGTT  TACACAAGAA  ATAAGTCGAA  ATTACCATT   TCCTATTTTT  1680
1681  AACCTGTGTT  TTGTATCATA  ATGGACATGC  GGAATTTTTA  TTTTGTACTT  ACTACGTATT  1740
1741  CTTTGCAAGG  AGTATTGTAA  ATTTTACTGG  CAATTATTAT  TGTACTATTC  TAATGTAAGA  1800
1801  TTTTTACACT  TTTTTTCAGA  AATAAAATGC  TTAATTTTCA  AAGAAAAAAA  AAAAAAAAAA  1860
                  |          |          |          |          |          |
                  10         20         30         40         50         60
```

FIG. 11

BF-3 mouse cDNA

DNA sequence 1155 b.p. TCTAGGCTCCAC ... TGAGCCCAGCGG linear

```
             10         20         30         40         50         60
   1 TCTAGGCTCC ACGGTCGCGC GTGGCGTCTG TGCCGCCAGC TCAGGGCTGC CACCCGCCAA   60
  61 GCCGAGAGTG CGCGGCCAGC GGGGCCGCCT GCCGTGCACC CTTCAGGATG CCGATCCGCC  120
 121 CGGTCGCTGA ACCCGAGCGC CGGCGTCTTC CGGCGGTGGA CCGGAGGCT GCCCCGAGTC  180
 181 GGGGCTGCCT GCATCGCTCC GTCCCTTCCT GCTCTCCTGC TCCGGGCCTC GCTCGCCCGG  240
 241 GGCCGCAGTC GGTGCGCGCA GCCGGCGACC GGCGGTCTGG GACACAGCAT GCAGGCGCGT  300
 301 TACTCGGTAT CGGACCCCAA CACCCTGGGA GTGGTACCCT ATTTGAGTGA GCAAAACTAC  360
 361 TACCGGGCGG CCGGCAGCTA CGGCGGCATG TGGGCGTCTA CTCCGGCCAC CTCCGGCCAC  420
 421 CCGGAGCAGT ACGGCGCCCG CATGGGCCGC GCCAGCCCCA CCTACCACCA TCAGCCCTTT  480
 481 TCTCCCAAGG ACCTGGTGAA GCCGCCCTAC AGCTATATAG CGCTCATCAC CATGGCGATC  540
 541 CAGAACGCGC CAGAGAAGAA CAAGCAGGGC AACGGCATCT ACCAGTTCAT CATGGACCGT  600
 601 TTCCCTTCT ACCGCGAGAA CAAGCAGGGC TGGCAGAACA GCATCCGCCA CAACCTGTCA  660
 661 CTCAATGAGT GCTTCGTGAA AGTGCCGCGC GACGACAAGA AGCCGGGCAA GGGCAGCTAC  720
 721 TGGACGCTCG ACCCGGACTC CTACAACATG TTCGAGAATG GCAGCTTCCT GCGGCGCCGG  780
 781 CGGCGGCTTC AGAAGAAGGA TGTGCCCAAG GACAAGGAGG AGCGGGCCCA CCTCAAGGAG  840
 841 CCGCCCTCGA CCACGGCCAA GGGCGCTCCG ACAGGGACCC CGGTAGCTGA CGGGCCCAAG  900
 901 GAGGCCGAGA AGAAAGTCGT GGTTAAGAGC GAGGCCGGCG CCCCCGCACT GCCGGTCATC  960
 961 ACCAAGGTGG AGACGCTGAG CCCCGAGGGA GCGCTGCAGG CCAGTCCCGC CAGGCATCC 1020
1021 TCCACGCCCG CAGTGTCCCC AGACGGCTCG CTGCCCGAGC ACCACGCCGC GGCGCCTAAC 1080
1081 GGGCTGCCCG GCTTCAGCGT AGAAGAAGGA GGTTAAGAGC GAGGCCGGCG CCCCCGCACT 1140
1141 ATCTGAGCCC AGCGG                                                  1155
             10         20         30         40         50         60
```

FIG. 13

EcoR I  Bgl II          Not I
└┴──────────────┘                    pBSKS-BF-2

BF-3

SEQUENCE LISTING

```
(1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 2830 base pairs
        (B) TYPE: nucleic acid
        (C) STRANDEDNESS: single
        (D) TOPOLOGY: linear (ii) MOLECULE TYPE: cDNA (iii) HYPOTHETICAL: N (iv) ANTI-SENSE: N (ix) FEATURE:
        (A) NAME/KEY: CDS
        (B) LOCATION: 443..1882
        (D) OTHER INFORMATION:

(ix) FEATURE:
        (A) NAME/KEY: misc_feature
        (B) LOCATION: 926..1255
        (D) OTHER INFORMATION: /note= "nucleotide sequence
            encoding DNA binding domain
            homology"

(ix) FEATURE:
        (A) NAME/KEY: misc_signal
        (B) LOCATION: 1883..1885
        (D) OTHER INFORMATION: /note= "translation termination
            codon"

(xi) SEQUENCE DESCRIPTION: SEQ ID NO:1:

GGCGGCCGCT CCGGGACGCG CCCGCGCGCT GCCCGGCTCT CCCCCCCTTC GGGCTGCCGC      60

TGCTGCTGCT GTGACTGCTG CGGCGCGAGG AGGAGGAGGC AGCGGGGGAG GGGGAGGCCG     120

GGCGCGGAAC GGAGCGGGGC GCTGCACCCC GGGCGACGGG TTGCTTCTGC CTCTAGCTTC     180

TCTCTCTCTC TCTCTCTCTC TCTCTCTCTC TCTCTCTCTC TCTCTCTCTC TCTCTCTCTC     240

TAATTCTTGA GGGGTGGTTG CAGCTTTTGC TACATGCCTT GCCAGCGCCG GAGCCTGCGG     300

TCCAACTGCG CTGCTGCCGG AGCGCTCAGT GCCGCCCCCG CTGCCCGCTC CCCCCGCTCC     360
```

```
CCACTCCGAA CCCGCCGGTC GCTCGCCGCG CTGCTGCTCG GCTCCTGCGC CGCCGCCGTC      420

GCCCCCCCCC GACGCCTGGG TG ATG CTG GAC ATG GGA GAT AGG AAA GAG GTG      472
                        Met Leu Asp Met Gly Asp Arg Lys Glu Val
                         1               5                  10

AAA ATG ATT CCC AAG TCC TCG TTC AGC ATC AAC AGC CTG GTC CCT GAG      520
Lys Met Ile Pro Lys Ser Ser Phe Ser Ile Asn Ser Leu Val Pro Glu
             15                  20                  25

GCC GTC CAG AAC GAC AAC CAC CAC GCG AGC CAC GGC TAC CAC AAC AGC      568
Ala Val Gln Asn Asp Asn His His Ala Ser His Gly Tyr His Asn Ser
             30                  35                  40

CAC CAC CCC CAG CAT CAC CAT CAT CAC CAC CAC CAC CCG CCG              616
His His Pro Gln His His His His His His His His Pro Pro
             45                  50                  55

CCG CCC GCG CCT CAG CCG CCG CCA CCG CCG CCC CAG CAG CAG CAG CAG      664
Pro Pro Ala Pro Gln Pro Pro Pro Pro Pro Pro Gln Gln Gln Gln Gln
         60                  65                  70

CCG CCC CCG GCC CCG CAG CCC CCG CAG GCG CGC GGC GCC CCA GCA GCG      712
Pro Pro Pro Ala Pro Gln Pro Pro Gln Ala Arg Gly Ala Pro Ala Ala
     75                  80                  85                  90

GAC GAC GAC AAG GGC CCC CAG CCG CTT CTG CTC CCG CCG TCC GCC GCC      760
Asp Asp Asp Lys Gly Pro Gln Pro Leu Leu Leu Pro Pro Ser Ala Ala
             95                  100                 105

CTG GAC GGG GCC AAG GCT GAC GCA CTT GGA GCC AAA GGC GAG CCA GGC      808
Leu Asp Gly Ala Lys Ala Asp Ala Leu Gly Ala Lys Gly Glu Pro Gly
             110                 115                 120

GGC GGG CCT GCG GAG CTG GCG CCC GTC GGG CCG GAC GAG AAG GAG AAG      856
Gly Gly Pro Ala Glu Leu Ala Pro Val Gly Pro Asp Glu Lys Glu Lys
             125                 130                 135

GGC GCG GGC GCT GGG GGG GAG GAG AAG AAG GGG GCG GGC GAG GGC GGC      904
Gly Ala Gly Ala Gly Gly Glu Glu Lys Lys Gly Ala Gly Glu Gly Gly
     140                 145                 150

AAG GAC GGG GAG GGG GGC AAG GAG GGC GAC AAG AAC AAC GGC AAG TAC      952
Lys Asp Gly Glu Gly Gly Lys Glu Gly Asp Lys Asn Asn Gly Lys Tyr
155                 160                 165                 170

GAG AAG CCG CCG TTC ACC TAC AAC GCG CTC ATC ATG ATG GCC ATC AGG      1000
Glu Lys Pro Pro Phe Thr Tyr Asn Ala Leu Ile Met Met Ala Ile Arg
             175                 180                 185

CAG AGT CCC GAG AAG CGC CTG ACG CTC AAC GGC ATC TAC GAG TTC ATC      1048
Gln Ser Pro Glu Lys Arg Leu Thr Leu Asn Gly Ile Tyr Glu Phe Ile
             190                 195                 200

ATG AAG AAC TTC CCT TAC TAC CGC GAG AAC AAG CAG GGC TGG CAG AAC      1096
Met Lys Asn Phe Pro Tyr Tyr Arg Glu Asn Lys Gln Gly Trp Gln Asn
             205                 210                 215

TCC ATC CGC CAC AAC CTG TCC CTC AAC AAG TGC TTC GTG AAG GTA CCG      1144
Ser Ile Arg His Asn Leu Ser Leu Asn Lys Cys Phe Val Lys Val Pro
         220                 225                 230

CGC CAC TAC GAC GAC CCG GGC AAG GGC AAC TAC TGG ATG CTG GAC CCG      1192
Arg His Tyr Asp Asp Pro Gly Lys Gly Asn Tyr Trp Met Leu Asp Pro
235                 240                 245                 250

TCG AGC GAC GAC GTG TTC ATC GGC GGC ACG ACC GGC AAG CTG CGG CGC      1240
Ser Ser Asp Asp Val Phe Ile Gly Gly Thr Thr Gly Lys Leu Arg Arg
             255                 260                 265

CGC TCC ACC ACG TCT CGG GCC AAG CTA GCC TTT AAG CGC CGG CCA CGG      1288
Arg Ser Thr Thr Ser Arg Ala Lys Leu Ala Phe Lys Arg Arg Ala Arg
             270                 275                 280

CTC ACC TCC ACC GGC CTC ACC TTC ATG GAC CGC GCC GGC TCC CTC TAC      1336
Leu Thr Ser Thr Gly Leu Thr Phe Met Asp Arg Ala Gly Ser Leu Tyr
             285                 290                 295

TGG CCC ATG TCG CCC TTC CTG TCC CTG CAC CAC CCT CGC GCC AGC AGC      1384
```

```
Trp Pro Met Ser Pro Phe Leu Ser Leu His His Pro Arg Ala Ser Ser
    300                 305                 310

ACT TTG AGT TAC AAC GGG ACC ACC TCG GCC TAC CCC AGC CAC CCC ATG      1432
Thr Leu Ser Tyr Asn Gly Thr Thr Ser Ala Tyr Pro Ser His Pro Met
315                 320                 325                 330

CCC TAC AGC TCC GTG TTG ACT CAA AAC TCG CTG GGC AAC AAC CAC TCC      1480
Pro Tyr Ser Ser Val Leu Thr Gln Asn Ser Leu Gly Asn Asn His Ser
                335                 340                 345

TTC TCC ACC GCC AAC GGG CTG AGC GTG GAC CGG CTG GTC AAC GGG GAG      1528
Phe Ser Thr Ala Asn Gly Leu Ser Val Asp Arg Leu Val Asn Gly Glu
            350                 355                 360

ATC CCG TAC GCC ACG CAC CAC CTC ACG GCC GCT GCG CTC GCC GCC TCC      1576
Ile Pro Tyr Ala Thr His His Leu Thr Ala Ala Ala Leu Ala Ala Ser
        365                 370                 375

GTG CCC TGC GGC CTG TCG GTG CCC TGC TCC GGG ACC TAC TCC CTC AAC      1624
Val Pro Cys Gly Leu Ser Val Pro Cys Ser Gly Thr Tyr Ser Leu Asn
380                 385                 390

CCC TGC TCC GTC AAC CTG CTC GCG GGC CAG ACC AGT TAC TTT TTC CCC      1672
Pro Cys Ser Val Asn Leu Leu Ala Gly Gln Thr Ser Tyr Phe Phe Pro
395                 400                 405                 410

CAC GTC CCG CAC CCG TCA ATG ACT TCG CAG ACC AGC ACG TCC ATG AGC      1720
His Val Pro His Pro Ser Met Thr Ser Gln Thr Ser Thr Ser Met Ser
                415                 420                 425

GCC CGG GCC GCG TCC TCC TCT ACG TCG CCG CAG GCC CCC TCG ACC CTG      1768
Ala Arg Ala Ala Ser Ser Ser Thr Ser Pro Gln Ala Pro Ser Thr Leu
            430                 435                 440

CCC TGT GAG TCT TTA AGA CCC TCT TTG CCA AGT TTT ACG ACA GGA CTG      1816
Pro Cys Glu Ser Leu Arg Pro Ser Leu Pro Ser Phe Thr Thr Gly Leu
        445                 450                 455

TCC GGG GGA CTG TCT GAT TAT TTC ACA CAT CAA AAT CAG GGG TCT TCT      1864
Ser Gly Gly Leu Ser Asp Tyr Phe Thr His Gln Asn Gln Gly Ser Ser
    460                 465                 470

TCC AAC CCT TTA ATA CAT TAACATCCCG GGACCAGAC TGTAAGTGAA              1912
Ser Asn Pro Leu Ile His
475                 480

CGTTTTACAC ACATTTGCAT TGTAAATGAT AATTAAAAAA TAAGTCCAGG TATTTTTTAT    1972

TAAGCCCTTC CCCCCATTTC TGTACGTTTG TTCAGTCTTT AGGGTTGTTT ACTATTCTAA    2032

CACGGTGTGG AGTGTCAGCA GCGAGGTGCA ATGTGGGAGA ATACATTGTA GAATATAAGG    2092

TTTGGACGTC AAATTATAGT AGAATGTGTA TCTAAATAGT GACTGCTTTG CCATTTCATT    2152

CAAACCTGAC AAGTCTATCT CTAAAGGCTG CCAGATTTCC ATGTGTGCAG TATTATAAGT    2212

TATCATGGAT CTATCTGGTG GACGCAGGCC TTGAAGAACA ACCTAAATTA TGAAGAGAGT    2272

TTTAAAATGT TAAACTGTAA TTTGAATGTA AGAATTTGTA GGTAAAGGTG CCCAAGAAAT    2332

TATATTGGCC ATTTATTGTT TTGTCCTTTT CTTTAAAGAA CTGTTTTTTT CTTTTGTTTA    2392

CTTTTAGACC AAAGATTGGA TTCTAGCAAA TGCACTTGGT ATACTAAGTA TTAAAACAAG    2452

CAAACAAACA AACAAAAAAA GGAAGGTTGT TTAGTTTGGC AACACTGCCC ATTCAATTGA    2512

ATCCGAAAGG ACAAAATTAA GGATTGCCTT CAGTTTGTGT TGTGTATATT TCGATGTATG    2572

TGGTCACTAA CAGGTCACTT TATTTTTTCT AAATGTAGTG AAATGTTAAT ACCTATTGTA    2632

CTTATAGGTA AACCTTGCAA ATATGTAACC TGTGTTGCGC AAATGCCGCA TCAATTTGAG    2692

TGATTGTTAA TGTTGCTTAA AAATTCTTGA TTGTGATACT GTGGTCATAT GCCCTTGTTT    2752

GTCACTTACA AAAATGTTTA CTATGAACAC ACAGAAATAA AAAATAGGCT AAATTCATAT    2812

ATAAAAAAAA AAAAAAAA                                                  2830
```

(2) INFORMATION FOR SEQ ID NO:2:

(i) SEQUENCE CHARACTERISTICS:
        (A) LENGTH: 480 amino acids
        (B) TYPE: amino acid
        (D) TOPOLOGY: linear (ii) MOLECULE TYPE: protein (xi) SEQUENCE DESCRIPTION: SEQ ID NO:2:

```
Met Leu Asp Met Gly Asp Arg Lys Glu Val Lys Met Ile Pro Lys Ser
 1               5                  10                  15

Ser Phe Ser Ile Asn Ser Leu Val Pro Glu Ala Val Gln Asn Asp Asn
                20                  25                  30

His His Ala Ser His Gly Tyr His Asn Ser His His Pro Gln His His
            35                  40                  45

His His His His His His His Pro Pro Pro Ala Pro Gln Pro
        50                  55                  60

Pro Pro Pro Pro Gln Gln Gln Gln Gln Pro Pro Ala Pro Gln
65                  70                  75                  80

Pro Pro Gln Ala Arg Gly Ala Pro Ala Ala Asp Asp Asp Lys Gly Pro
                85                  90                  95

Gln Pro Leu Leu Leu Pro Pro Ser Ala Ala Leu Asp Gly Ala Lys Ala
                100                 105                 110

Asp Ala Leu Gly Ala Lys Gly Glu Pro Gly Gly Gly Pro Ala Glu Leu
            115                 120                 125

Ala Pro Val Gly Pro Asp Glu Lys Glu Lys Gly Ala Gly Ala Gly Gly
        130                 135                 140

Glu Glu Lys Lys Gly Ala Gly Glu Gly Gly Lys Asp Gly Glu Gly Gly
145                 150                 155                 160

Lys Glu Gly Asp Lys Asn Asn Gly Lys Tyr Glu Lys Pro Pro Phe Thr
                165                 170                 175

Tyr Asn Ala Leu Ile Met Met Ala Ile Arg Gln Ser Pro Glu Lys Arg
                180                 185                 190

Leu Thr Leu Asn Gly Ile Tyr Glu Phe Ile Met Lys Asn Phe Pro Tyr
            195                 200                 205

Tyr Arg Glu Asn Lys Gln Gly Trp Gln Asn Ser Ile Arg His Asn Leu
        210                 215                 220

Ser Leu Asn Lys Cys Phe Val Lys Val Pro Arg His Tyr Asp Asp Pro
225                 230                 235                 240

Gly Lys Gly Asn Tyr Trp Met Leu Asp Pro Ser Ser Asp Val Phe
                245                 250                 255

Ile Gly Gly Thr Thr Gly Lys Leu Arg Arg Arg Ser Thr Thr Ser Arg
                260                 265                 270

Ala Lys Leu Ala Phe Lys Arg Arg Ala Arg Leu Thr Ser Thr Gly Leu
            275                 280                 285

Thr Phe Met Asp Arg Ala Gly Ser Leu Tyr Trp Pro Met Ser Pro Phe
        290                 295                 300

Leu Ser Leu His His Pro Arg Ala Ser Ser Thr Leu Ser Tyr Asn Gly
305                 310                 315                 320

Thr Thr Ser Ala Tyr Pro Ser His Pro Met Pro Tyr Ser Ser Val Leu
                325                 330                 335

Thr Gln Asn Ser Leu Gly Asn Asn His Ser Phe Ser Thr Ala Asn Gly
                340                 345                 350

Leu Ser Val Asp Arg Leu Val Asn Gly Glu Ile Pro Tyr Ala Thr His
            355                 360                 365
```

```
His Leu Thr Ala Ala Ala Leu Ala Ala Ser Val Pro Cys Gly Leu Ser
    370                 375                 380

Val Pro Cys Ser Gly Thr Tyr Ser Leu Asn Pro Cys Ser Val Asn Leu
385                 390                 395                 400

Leu Ala Gly Gln Thr Ser Tyr Phe Phe Pro His Val Pro His Pro Ser
                405                 410                 415

Met Thr Ser Gln Thr Ser Thr Ser Met Ser Ala Arg Ala Ala Ser Ser
                420                 425                 430

Ser Thr Ser Pro Gln Ala Pro Ser Thr Leu Pro Cys Glu Ser Leu Arg
            435                 440                 445

Pro Ser Leu Pro Ser Phe Thr Thr Gly Leu Ser Gly Gly Leu Ser Asp
    450                 455                 460

Tyr Phe Thr His Gln Asn Gln Gly Ser Ser Ser Asn Pro Leu Ile His
465                 470                 475                 480
```

(2) INFORMATION FOR SEQ ID NO:3:

(i) SEQUENCE CHARACTERISTICS:
        (A) LENGTH: 1860 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGCCTTGCCG AGCTCCGTTT CTAGATTCTC ACTCCTCCCG CGCCCTTCTG GGCGCCCGAC      60

ACCGACTGGC CCGCCAGGGT CCAGCCACCC CCTCCTGGAC TAACCGGGCT AAAGGGACCA     120

CAGTGGAAAA GGTCAAGTCT AGAGCGCCCG CCACCCGGTG CCCGCCGAGC CGGGGAGCGC     180

AAACACCTCG CACAGCCCTG CTCGCCAAGT AGCGGAGCGG AGGGGCCCCA GCCACCTCCT     240

GCAGCCGCGC GTCGCAGAGT GGCGTCCTCG CTCCGGGTCC GCCCCTCCGG GATCGGCCTG     300

GGGAGGCCAG GGAGCCGGGA GCCCGGTGCC CCTATGTGCC GCCGCGCCAC CGCGCCGCCC     360

CAGCTATGAC CCTGAGCACG GAGATGTCCG ATGCCTCCGG CCTCGCGGAG GAGACAGACA     420

TCGACGTGGT GGGGGAGGGC GAGGACGACG AGGAGGAGGA GGACGATGAC GACGAGGGCG     480

GCGGCGGCCG CGGCGGCGGC GGGTCCCGGT TGCCGAGCTC GGCCCAGCGG CGGAGGCGCT     540

CTTACGCCGG GGAGGTCGAT CTCGAGGACC TGGAGGAGGA GGACGACGAT GACCTGCTGC     600

TGGCCCCCCG GCCCGCCGCG TCCCCCGCGC CTCCGGGTCC TGCGCCCGCC CCGGGGACGG     660

GGTCGGGCGG CTGCAGCGGC GCCGGAGCGG GAGGCGGCGC GGGAGGTGGT ACGGGCGCGG     720

GCACGGGCGG GGGCGCTAAG AATCCGCTGG TGAAGCCGCC CTACTCGTAC ATCGCGCTCA     780

TCACCATGGC CATCCTGCAG AGCCCCAAGA AGCGCCTGAC GCTCAGCGAG ATCTGCGAGT     840

TCATCAGCAG CCGCTTCCCT TACTACCGGG AGAAGTTCCC CGCTTGGCAG AACAGCATCC     900

GTCACAACCT GTCGCTCAAC GACTGCTTCG TCAAGATCCC GCGCGAACCG GGCAACCCGG     960

GCAAGGGCAA CTACTGGACG CTCGACCCGG AGTCCGCAGA TATGTTCGAC AACGGCAGCT    1020

TCCTGCGGCG CCGCAAGCGC TTCAAGCGCC AGCCGCTACT CGATCCCGCG CTGGGGACTC    1080

TGCACCAAGG GACAGCGCTG TCCAGTGTGG AGAACTTTAC TGCTAGGATT CCAATTGTT     1140

AGGAACGTCG TTAGCGCGCG GGAGAGCGAA GGTAGGACTC CCGGCTTCTT TCTCCGGATG    1200

GGGGGGTTGG TTTCGTTCGC CCCTCCCGGT CCTCGGAGAC CCCGCGCCCC CCGTTTTCGC    1260

CGCTTCGGAT TCTTGGACCA GACTGTGTTG GGCGACAGCT GGGGCGCCGC GCAGTTTAGC    1320

TCAGAGGGTC CATCTATTTA TGCAAAATCG CCCTATGCTG CAACCCTGAC TTGGGGTGGG    1380
```

-continued

```
AAGGAGGGGA GTCGCTCTGT CTTGGCACTA GGAATTTCCT TGACTTTTGA CAAATTGAGA    1440

AAAAACAAAA CAAAACAAGC AAAATCATCA AAACTAAGCC CTTTTTGAGG TGTAGAGATT    1500

CACAGGTCCA GCGTTTTAAA AAATCAGTAA TGTTTAAATG CAGCTTATAG AAAACCAGTA    1560

AAAGTCTCCA AGAAATGCCT CTACTTGTTC ACACTTGTTT GGTAGACTTT TTTCATGGAA    1620

AGAAAAAAAA TTAACATGTT TACACAAGAA ATAAGTCGAA ATTTACCATT TCCTATTTTT    1680

AACCTGTGTT TTGTATCATA ATGGACATGC GGAATTTTTA TTTTGTACTT ACTACGTATT    1740

CTTTGCAAGG AGTATTGTAA ATTTTACTGG CAATTATTAT TGTACTATTC TAATGTAAGA    1800

TTTTTACACT TTTTTTCAGA AATAAAATGC TTAATTTTCA AGAAAAAAA AAAAAAAAAA    1860

(2) INFORMATION FOR SEQ ID NO:4:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TCTAGGCTCC ACGGTCGCGC GTGGCGTCTG TGCCGCCAGC TCAGGGCTGC CACCCGCCAA      60

GCCGAGAGTG CGCGGCCAGC GGGGCCGCCT GCCGTGCACC CTTCAGGATG CCGATCCGCC    120

CGGTCGCTGA ACCCGAGCGC CGGCGTCTTC CGCGCGTGGA CCGCGAGGCT GCCCCGAGTC    180

GGGGCTGCCT GCATCGCTCC GTCCCTTCCT GCTCTCCTGC TCCGGGCCTC GCTCGCCGCG    240

GGCCGCAGTC GGTGCGCGCA GCCGGCGACC GGGCGTCTGG GACACAGCAT GCAGGCGCGT    300

TACTCGGTAT CGGACCCCAA CACCCTGGGA GTGGTACCCT ATTTGAGTGA GCAAAACTAC    360

TACCGGGCGG CCGGCAGCTA CGGCGGCATG GCCAGCCCCA TGGGCGTCTA CTCCGGCCAC    420

CCGGAGCAGT ACGGCGCCGG CATGGGCCGC TCCTACGCGC CCTACCACCA TCAGCCCTTT    480

TCTCCCAAGG ACCTGGTGAA GCCGCCCTAC AGCTATATAG CGCTCATCAC CATGGCGATC    540

CAGAACGCGC CAGAGAAGAA GATCACTCTG AACGGCATCT ACCAGTTCAT CATGGACCGT    600

TTCCCCTTCT ACCGCGAGAA CAAGCAGGGC TGGCAGAACA GCATCCGCCA CAACCTGTCA    660

CTCAATGAGT GCTTCGTGAA AGTGCCGCGC GACGACAAGA AGCCGGGCAA GGGCAGCTAC    720

TGGACGCTCG ACCCGGACTC CTACAACATG TTCGAGAATG GCAGCTTCCT GCGGCGGCGG    780

CGGCGCTTCA AGAAGAAGGA TGTGCCCAAG GACAAGGAGG AGCGGGCCCA CCTCAAGGAG    840

CCGCCCTCGA CCACGGCCAA GGGCGCTCCG ACAGGGACCC CGGTAGCTGA CGGGCCCAAG    900

GAGGCCGAGA AGAAAGTCGT GGTTAAGAGC GAGGCGGCGT CCCCCGCACT GCCGGTCATC    960

ACCAAGGTGG AGACGCTGAG CCCCGAGGGA GCGCTGCAGG CCAGTCCGCG CAGCGCATCC   1020

TCCACGCCCG CAGTGTCCCC AGACGGCTCG CTGCCGGAGC ACCACGCCGC GGCGCCTAAC   1080

GGGCTGCCCG GCTTCAGCGT GGAGACCATC ATGACGCTGC GCACGTCGCC TCCGGGGGCG   1140

ATCTGAGCCC AGCGG                                                     1155
```

BRAIN TRANSCRIPTION FACTORS, NUCLEIC ACIDS ENCODING SAME AND USES THEREOF

This application is a continuation-in-part of U.S. application Ser. No. 07/882,292, filed May 13, 1992, now U.S. Pat. No. 5,324,638 the contents of which are hereby incorporated by reference.

BACKGROUND OF THE INVENTION

Throughout this application various references are referred to within parenthesis. Disclosures of these publications in their entireties are hereby incorporated by reference into this application to more fully describe the state of the art to which this invention pertains. Full bibliographic citation for these references may be found at the end of this application, preceding the sequence listing and the claims.

One of the important early events in the development of the mammalian central nervous system is the establishment of regional diversity along the neural tube under the influence of signals from the underlying mesoderm (Mangold 1933; Spemann 1938; Placzek et al. 1990). The caudal portion of the neural tube gives rise to the spinal cord while the rostral part develops into the brain. Morphologic studies have identified the initial subdivision of the developing brain into three vesicles, the forebrain, midbrain and hindbrain. The forebrain and hindbrain subsequently each subdivide, resulting in the five major regions of the brain. The most rostral region, the telencephalon, gives rise to the structures of the cerebral hemispheres which include the cerebral cortex and basal ganglia (Kandel et al. 1991). This subdivision of the developing brain is apparent initially as changes in the shape of the neuroepithelium, and is established prior to differentiation of the progenitor cells into neurons and glia (McKay 1989).

Our understanding of the molecular events which establish the regional subdivision of the brain during mammalian development have been aided by several approaches. Because development depends on the expression of genes in distinct spatial and temporal patterns, one approach has been the study of transcription factors which control gene expression in a cell or tissue-specific fashion. Another approach is the identification of mammalian homologs of Drosophila genes which have been established to play crucial roles in insect development (Kessel and Gruss 1990). For example, homeobox gene complexes in Drosophila and mammals are strikingly similar in structural organization and expression pattern along the A-P axis of the organism (Duboule and Dolle 1989; Graham et al. 1989). While recent findings of restricted expression in the developing brain of several homeodomain and one zinc finger proteins have provided insight into the development of the hindbrain (Murphy et al. 1989; Wilkinson et al. 1989; Wilkinson et al. 1989; Hunt et al. 1991). The molecular basis of forebrain development remains poorly understood.

We have recently described a novel family of transcriptional activators, the HNF-3 family, whose members function to stimulate expression of a group of liver-specific genes. The expression of these factors in the mature animal is limited to tissues which derive from the gut endoderm such as the liver, lung and intestine (Lai et al. 1991). These findings suggested that HNF-3 family members might play a significant role in the development of these tissues. This hypothesis was supported when we learned that HNF-3 proteins were highly homologous to a Drosophila protein, fork head, which had been shown to be critical to normal fly development and to be expressed in the cells which were to form the insect gut structures (Weigel et al. 1989; Weigel and Jackle 1990). In this paper we described the discovery of a new member of the HNF-3/fork head family of transcription factors which is unique in that its expression is restricted to the telencephalon of the developing rat brain. Expression is readily detectable by embryonic day 10 in the area of the neural tube which gives rise to the telencephalic vesicles suggesting a critical role for this factor in the development of this region of the forebrain.

SUMMARY OF THE INVENTION

This invention provides an isolated, animal nucleic acid molecule encoding the Brain Factor-1, Brain Factor-2 and Brain Factor-3.

This invention also provides methods of detecting the expression of these Brain Factors. This invention also provides expression vectors to the Brain Factors.

This invention provides purified, animal Brain Factor-2 and animal Brain Factor-3.

This invention also provides antibodies of these Brain Factors and the uses of these antibodies to detect Brain Factors.

Finally, this invention provides a DNA vector which comprises the 5' nontranscribed region of the Brain Factor-1 gene, 3' nontranscribed region of the Brain Factor-1 gene and a gene of interest, linked operably.

BRIEF DESCRIPTION OF THE DRAWINGS

FIGS. 1A–1C Nucleic acid sequence of BF-1 (Seq.I.D. Nos. 1 and 2). The protein sequence is shown below beginning with the initiator methionine at base 443. The DNA binding domain homology extends from amino acid 162–271. Underlined amino acids are identical to those in the DNA binding domain of at least two of the four previously identified members of the HNF-3/fork head family.

FIGS. 5A–5K Expression pattern of BF-1 during rat development assessed by in-situ hybridization with an antisense probe (A–H, J–M). Pairs of photomicrographs and the corresponding autoradiograph from a transverse section of an E11.5 embryo (A, B), sagittal section of an E15 embryo (C, D) and a sagittal section of an E17 brian (E, F). Arrowheads in E indicate the approximate level of coronal sections (G,H) whose autoradiographs are shown. I is a representative control autoradiograph of a section parallel to that shown in E, hybridized with the corresponding sense probe for BF-1. J and K are autoradiographs of sagittal and coronal sections from adult brain. t, Telencephalon; d, diencephalon; ms, mesencephalon; mt, metencephalon; my, myelencephalon; s, spinal cord; cor, cerebral cortex; cb, cerebellum; cp, caudate putamen; h, hippocampus; tv, telencephalic vesicle; lv, lateral ventricles; op, optic stalk; r, retinal neuroepithelium; olf, olfactory placode; ole, olfactory epithelium; fg, foregut.

Figure 5A:
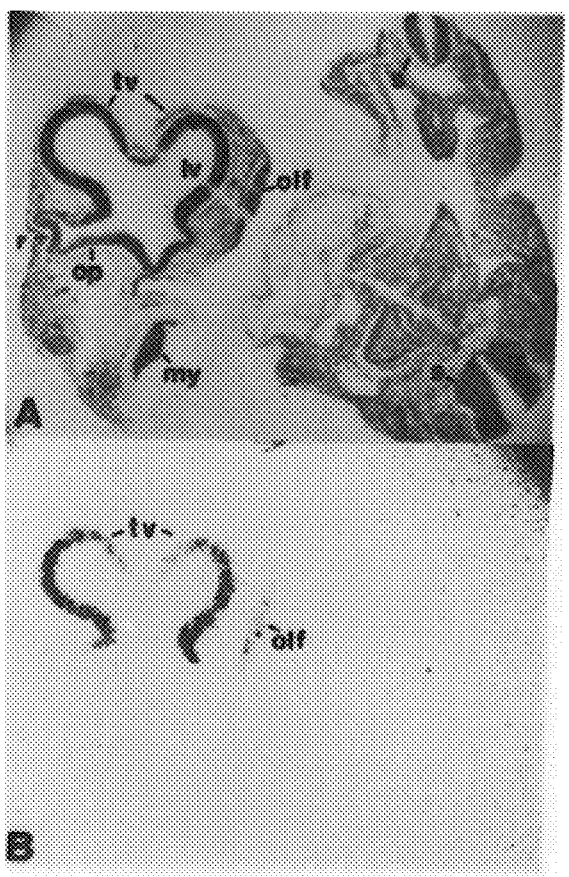
Figure 6A:
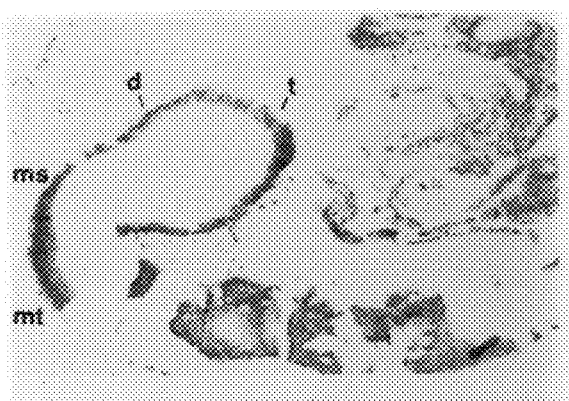
Figure 6B:
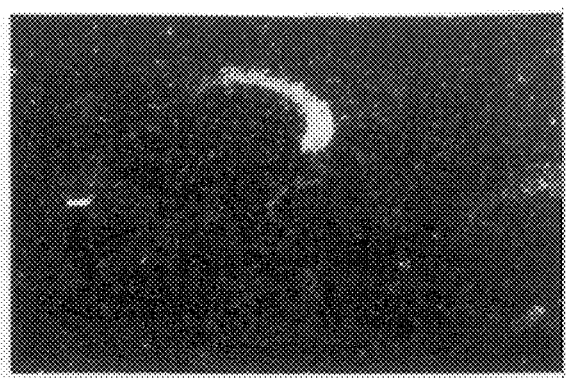
Figure 6C:
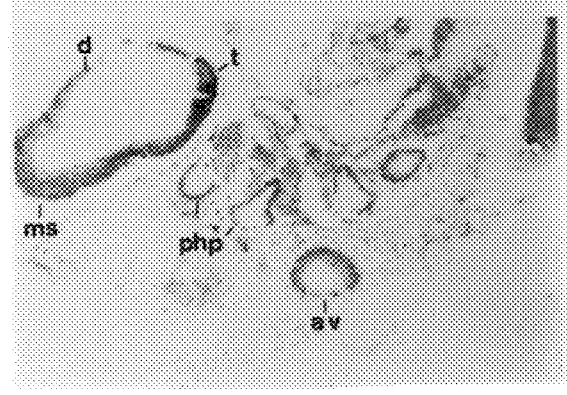

FIGS. 6A–6C Restriction of BF-1 expression to the telecephalon of the developing brain. Brightfield and darkfield photomicrographs of sections hybridized with a BF-1 antisense probe. A an B) Sagittal section from E10 with hybridization signal over the rostral end of the neural tube. C and B) Parasagittal section from E10 again with signal over the rostral neural tube as well as the auditory vesicle and pharyngeal pouches. C) Transverse section from E11.5 caudal to the section shown in FIG. 5A. t, telencephalon; d, diencephalon; Ms, mesencephalon; av, auditory vesicle; php, pharyngeal pouches; olf, olfactory placode; r, retinal neuroepithelium; sb, superior bridge.

Figure 7A:
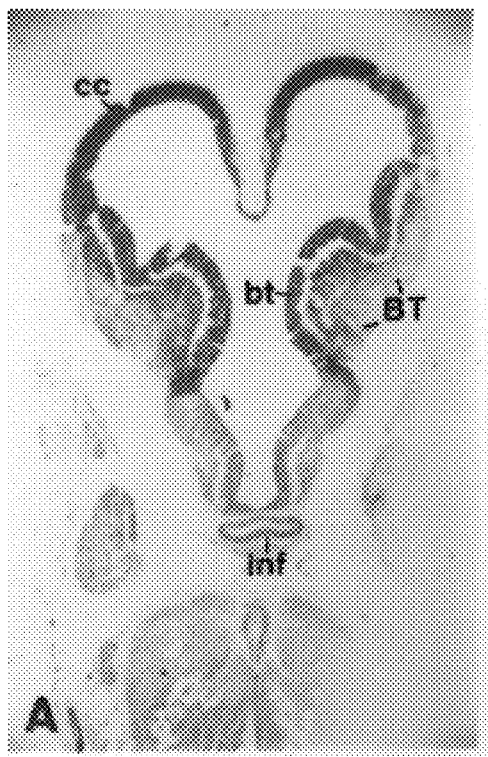
Figure 7B:
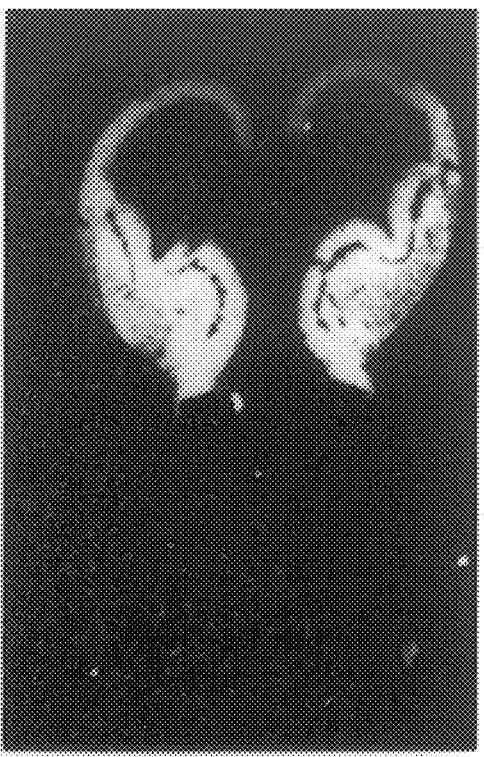
Figure 7C:
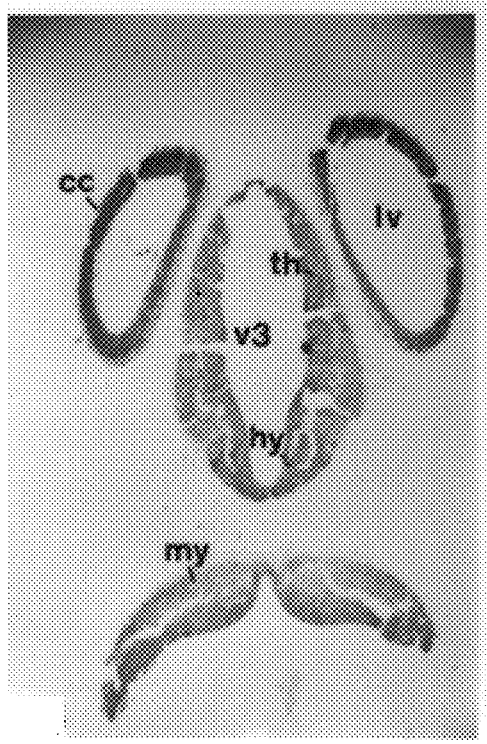
Figure 7D:

FIGS. 7A and 7D Restriction of BF-1 expression to the telencephalon at embryonic day 13.5. Brightfield and darkfield photomicrographs of sections hybridized with a BF-1 antisense probe. A and B) Transverse section from E13.5 with hybridization signal over the cerebral cortical neuroepithelium, the basal telencephalic neuroepithelium and the differentiating basal telencephalon. C and D) Transverse section rostral to that in A with hybridization over the cerebral cortical neuroepithelium. No detectable signal over the thalamic and hypothalamic neuroepithelium. cc, Cerebral cortical neuroepithelium; bt, basal telencephalic neuroepithelium; BT, basal telencephalon(Differentiating); inf, infundibulum; th, thalamus; hy, hypothalamus; my, myelencephalon; lv, lateral ventricle; v3, third ventricle.

Figure 8:
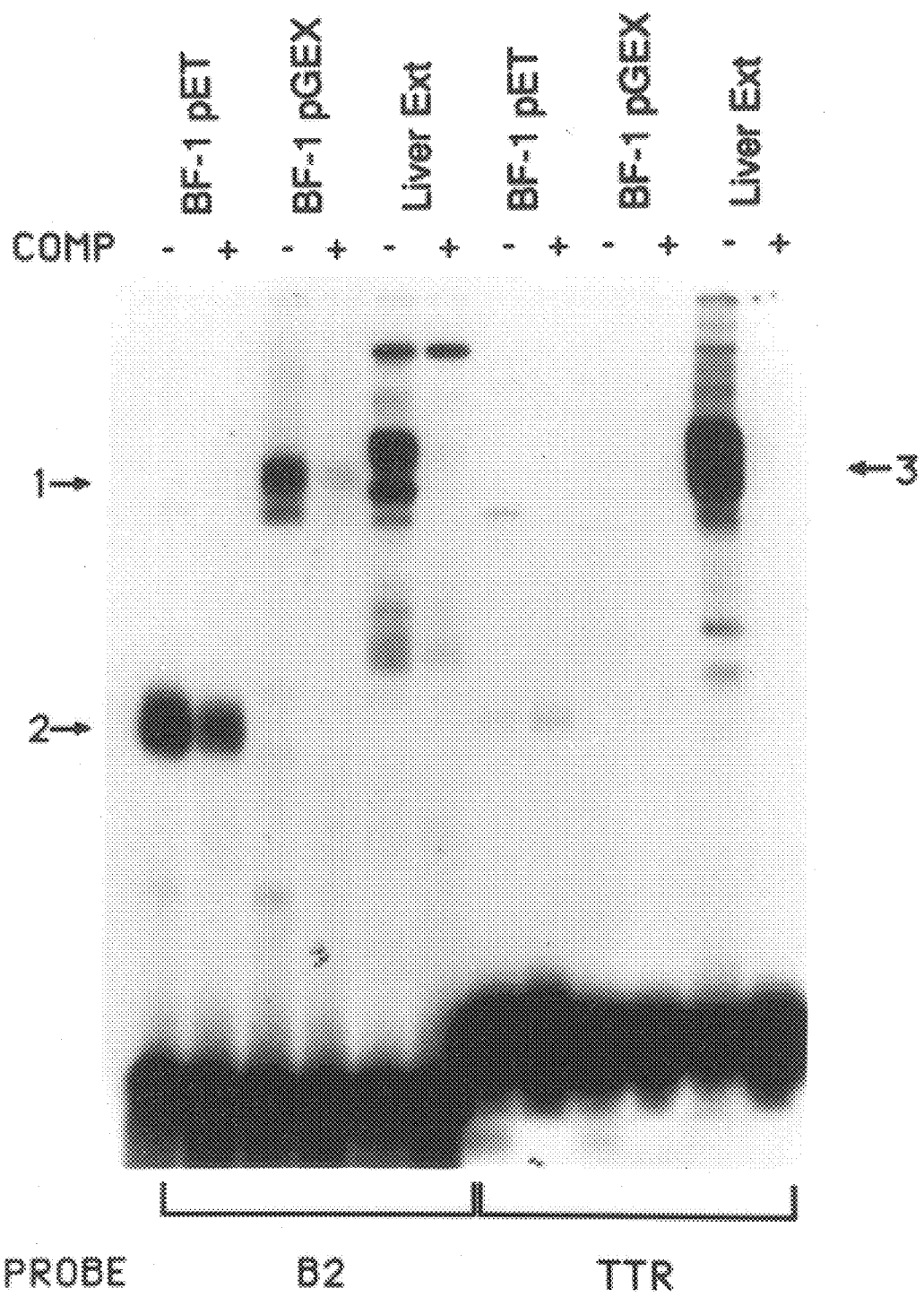

FIG. 8 Sequence specific binding of BF-1. Autoradiograph of a gel mobility shift assay comparing two BF-1 fusion proteins and liver extract using two different labeled probes, B2 site from the HNF-1 promoter and TTR from the transthyretin promoter. 1) BF-1 pGEX-DNA complex with the B2 probe, 2) BF-1 pET-DNA complex with the B2 probe, 3) the three complexes in liver extract from HNF-3a, 3b and 3g with both B2 and TTR probes. Alternate lanes include (–) no competitor or (+) 40-fold molar excess of unlabeled homologous competitor.

Figure 9:
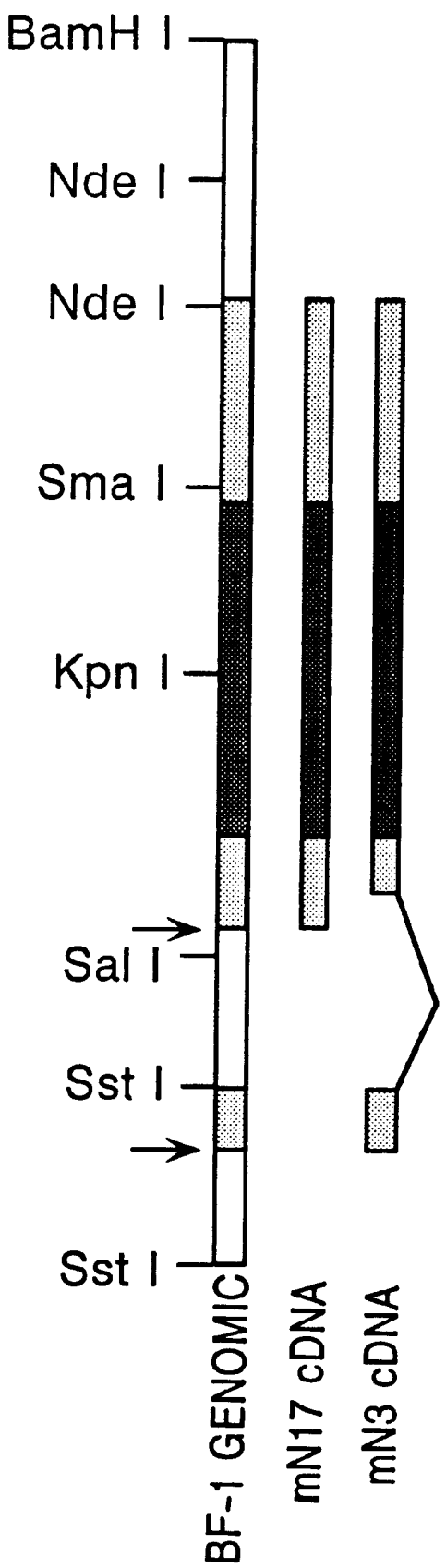

FIG. 9 Restriction map of BF-1 genomic DNA and two alternatively spliced cDNA.

FIGS. 10A and 10B BF-2 (Brain Factor-2) cDNA sequence (Seq.I.D. No.3).

FIG. 11 BF-3 (Brain Factor-3) cDNA sequence (Seq.I.D. No.4).

Figure 12:
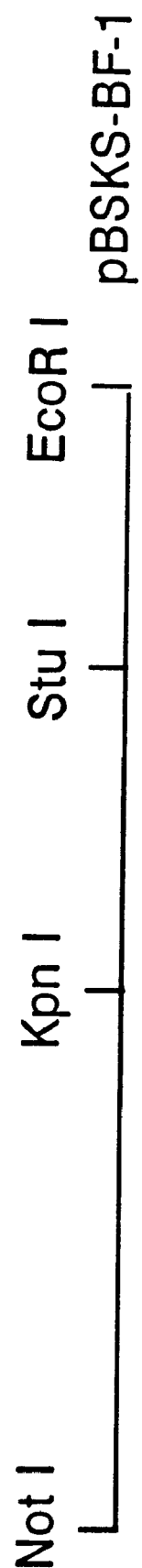

FIG. 12 Rat BF-1 cDNA Maps. This cDNA was cloned into EcoRI and NotI sites of pBluescript KS plasmid vector and can be excised using these restriction enzymes. The plasmid made is designated, pBSKS-BF-1. Also shown are additional unique restriction sites. The map is not drawn to scale.

Figure 13:
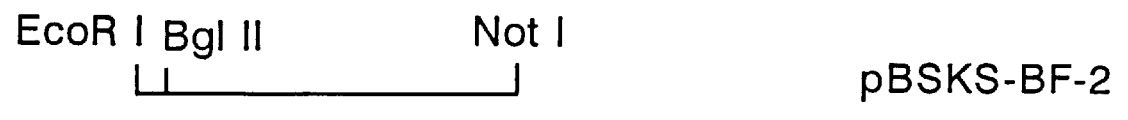

FIG. 13 Rat BF-2 cDNA Maps. This cDNA was cloned into EcoRI and NotI sites of pBluescript KS plasmid vector and can be excised using these restriction enzymes. The plasmid made is designated, pBSKS-BF-2. Also shown are additional unique restriction sites. The map is not drawn to scale.

Figure 14:
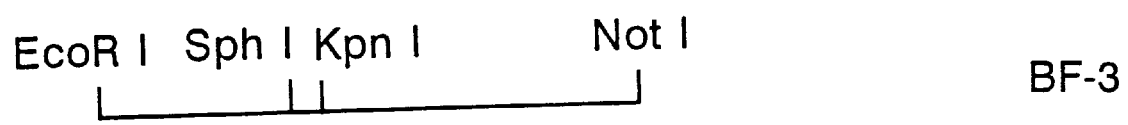

FIG. 14 Rat BF-3 cDNA Maps. This cDNA were cloned into EcoRI and NotI sites of pBluescript KS plasmid vector and can be excised using these restriction enzymes. The plasmid made is designated, BF-3. Also shown are additional unique restriction sites. The map is not drawn to scale.

Figure 15:
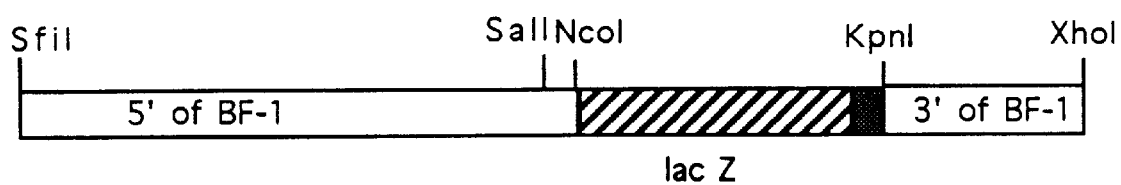

FIG. 15 Map of the Bf-1-lacZ expression cassette in plasmid pTBL3. Sfil and Xhol linkers were introduced into the Sphl and EcoRI sites of the vector, pGEM4 respectively. Then whole BF-1-lacZ expression cassette was cloned into the Sfil and Xhol sites of the modified vector. Ncol and Kpnl are not unique sites.

Figure 16:
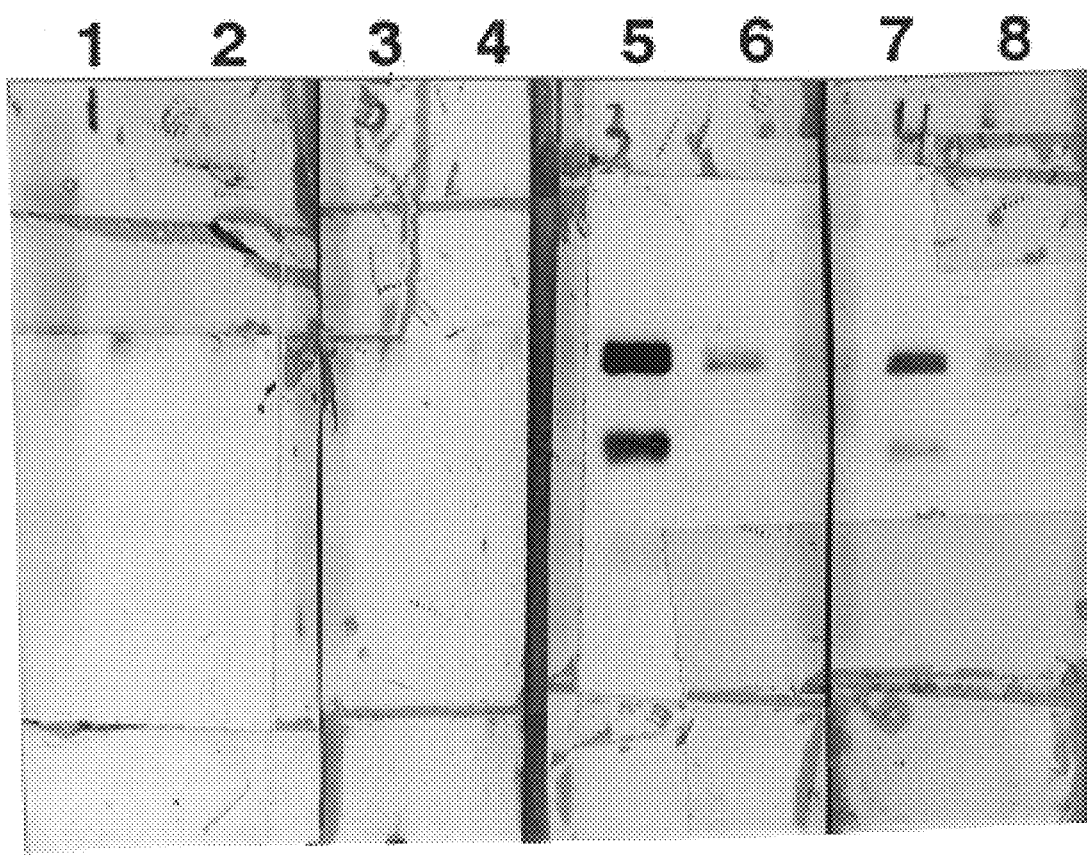

FIG. 16 Western analysis of BF-1 peptide antiserum. Partially purified BF-1 fusion protein run on SDS-PAGE gel and transferred to nitrocellulose. Lanes 1, 3, 5, 7 have 100 ng and lanes 2, 4, 6, 8 have 5 ng of BF-1. Lanes 1–2)1:2000 pre-immune serum. Lanes 3–4)1:20,000 pre-immune serum. Lanes 5–6)1:2000 BF-1 peptide antiserum. Lanes 7–8)1:20,000 BF-1 peptide anti serum. Arrowhead marks position of BF-1 fusion protein. The lower band represents a proteolytic fragment.

Figure 17:
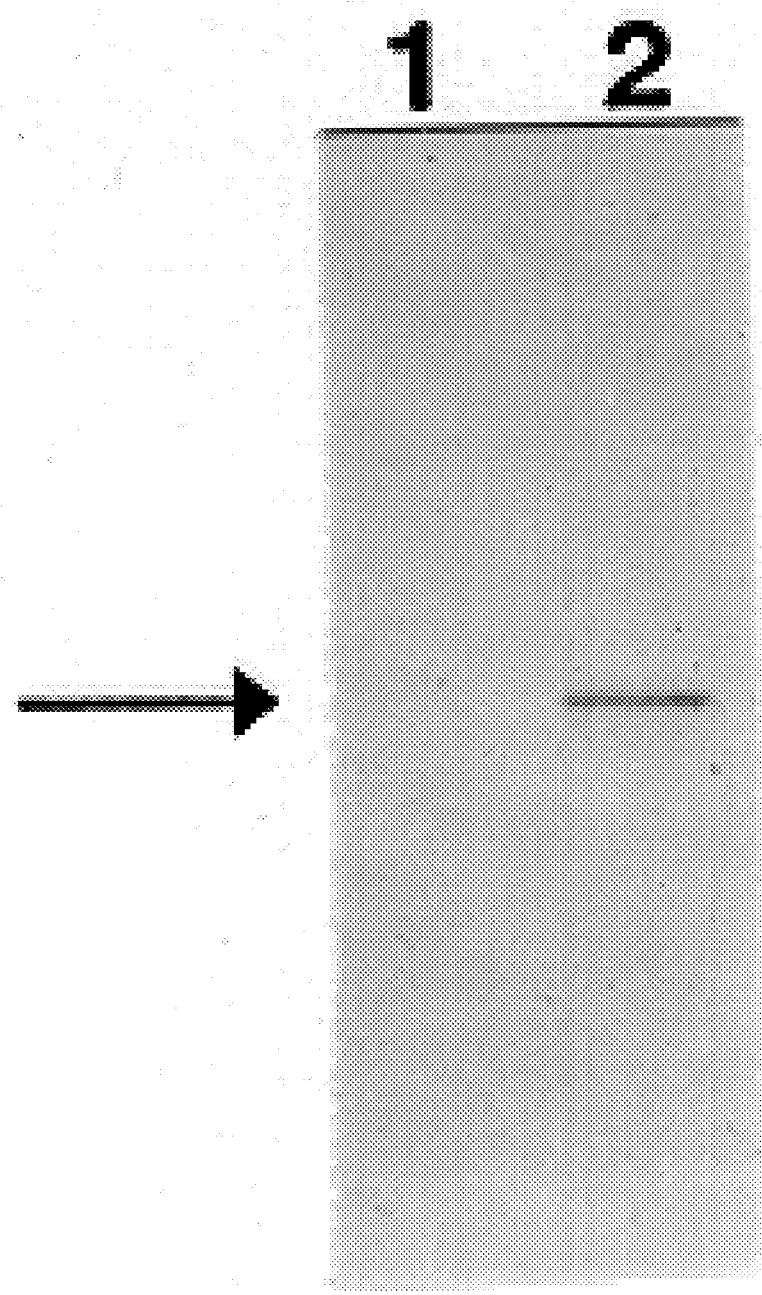

FIG. 17 SDS-PAGE analysis of immunoprecipitates of S-35 labeled reticulocyte lysates containing BF-1 incubated with rabbit serum; lane 1 preimmune serum; lane 2 BF-1 peptide antiserum. BF-1 bound to antibodies are precipitated with Staph A-agarose beads.

DETAILED DESCRIPTION OF THE INVENTION

This invention provides an isolated, animal nucleic acid molecule encoding the Brain Factor-1. This invention also provides an isolated, animal nucleic acid molecule encoding the Brain Factor-2. This invention further provides an isolated, animal nucleic acid molecule encoding the Brain Factor-3.

In an embodiment, the above described nucleic acid molecules are RNA. In another embodiment, the nucleic acid molecules are DNA. In a further embodiment, the DNA molecules are genomic. In a still further embodiment, the DNA molecules are cDNAs.

As used herein, the Brain Factors are Brain Factor-1, Brain Factor-2 and Brain Factor-3.

In an embodiment, the cDNA molecule has the nucleotide sequence substantially the same as the nucleotide sequence shown in FIGS. 1A–1C (Seq. I.D. No. 1). In another embodiment, the cDNA has the nucleotide sequence substantially the same as the nucleotide sequence shown in FIGS. 10A and 10B (Seq.I.D. No.3). In a further embodiment, the cDNA has the nucleotide sequence substantially the same as the nucleotide sequence shown in FIG. 11 (Seq.I.D. No.4).

This invention also provides plasmids which comprise the above described cDNA molecules.

In an embodiment, the rat BF-1 cDNA is cloned into the EcoRI and NotI sites of pBluescript KS plasmid and the resulting plasmid is designated, pBSKS-BF-1. This plasmid, pBSKS-BF-1, was deposited on Apr. 30, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pBSKS-BF-1, was accorded ATCC Accession Number 75459.

In another embodiment, the rat BF-2 is cloned into the EcoRI and NotI sites of pBluescript KS plasmid and the resulting plasmid is designated, pBSKS-BF-2. This plasmid, pBSKS-BF-2, was deposited on Apr. 30, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pBSKS-BF-2, was accorded ATCC Accession Number 75460.

In still another embodiment, the rat BF-3 cDNA is cloned into the EcoRI and NotI sites of pBluescript KS plasmid and the resulting plasmid is designated, BF-3. This plasmid, BF-3, was deposited on Apr. 30, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, BF-3, was accorded ATCC Accession Number 75461.

This invention also provides a nucleic acid probe comprising a nucleic acid molecule of about 15 nucleotides capable of specifically hybridizing with a sequence included within the sequence of a nucleic acid molecule encoding Brain Factor-1, Brain Factor-2 or Brain Factor-3.

The nucleic acid probe produced can either be DNA or RNA. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes the Brain Factor into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting a Brain Factor sequence downstream of a bacteriophage promoter such as T3, T7 or SP6. Large amounts of RNA probe may be produced by incubating the labeled nucleotides with the linearized Brain Factor fragment where it contains an upstream promoter in the presence of the appropriate RNA polymerase.

The current invention further provides a method to measure the expression of a Brain Factor in a cell. The probes synthesized above may be used to detect expression of a Brain Factor by detecting the presence of mRNA coding for the Brain Factor. Total mRNA from the cell may be isolated and contacting the mRNA so obtained with Brain Factor nucleic acid probe under hybridizing conditions. The presence of mRNA hybridized to the probe can be determined by gel electrophoresis or other methods known in the art. By measuring the amount of the hybrid made, the expression of the Brain Factor by the cell can be determined.

In one embodiment of this invention, nucleic acids are extracted by precipitation from lysed cells and the mRNA is isolated from the extract using an oligo-dT column which binds the poly-A tails of the mRNA molecules. The mRNA is then exposed to radioactively labelled probe on a nitrocellulose membrane, and the probe hybridizes to and thereby labels complementary mRNA sequences. Binding may be detected by luminescence autoradiography or scintillation counting. However, other methods for performing these steps are well known to those skilled in the art, and the discussion above is merely an example.

This invention further provides another method to measure the expression of the Brain Factors. The probes are also useful for in-situ hybridization or in order to locate tissues which express this gene, or for other hybridization assays for the presence of this gene or its mRNA in various biological tissues. The in-situ hybridization using a nucleic acid probe is well known in the art. Essentially, tissue sections are incubated with the nucleic acid probe to allow the hybridization to occur. Since the probe will carry a marker for the detection, the amount of the hybrid will be determined and so will the expression of the Brain Factor.

This invention further provides a method of detecting the expression of a Brain Factor in an animal tissue which comprises: (i) obtaining a sample from the animal tissue; (ii) contacting the sample with a labelled probe of either Brain Factor-1, Brain Factor-2 or Brain Factor-3 under conditions permitting the probe to bind to mRNA encoding the Brain Factor; (iii) removing unbound probe from the sample; and (iv) detecting the presence of bound, labelled probe in the sample, said presence indicating the expression of the Brain Factor in the animal tissue.

This invention also provide a method of detecting expression of a Brain Factor in an animal tissue by detecting the presence of mRNA coding for the Brain Factor which comprises: (i) obtaining mRNA sample from the animal tissue; (ii) contacting the obtained mRNA sample with a labelled probe of Brain Factor-b 1,Brain Factor-2 or Brain Factor-3 under conditions permitting the probe to bind to mRNA encoding the Brain Factor; (iii) removing unbound probe from the sample; and (iv) detecting the presence of bound, labelled probe in the sample, said presence indicating the expression of the Brain Factor in the animal tissue.

This invention also provides a method of diagnosing the abnormal expression of Brain Factor-1 in telencephalon-derived tissue or a tumor tissue from an animal which comprises the steps of:(i) obtaining a sample of telencephalon-derived tissue or a sample of tumor from the animal; (ii) contacting the tissue sample with a labelled probe of Brain Factor-1 conditions permitting the probe to bind to mRNA in the sample; (iii) removing unbound probe from the sample; (iv) detecting the presence of bound, labelled probe in the sample; (v) quantifying the amount of bound, labelled probe in the sample; and (vi) comparing the amount of bound, labelled probe in the sample to the amount of labelled probe which binds to a sample of non telencephalon-derived tissue or of telencephalon-derived tissue from a subject which expresses normal levels of the Brain Factor-1 in such tissue.

This invention also provides a method of diagnosing the abnormal expression of Brain Factor-1 in telencephalon-derived tissue or a tumor tissue from an animal which comprises:(i)obtaining mRNA sample from the telencephalon-derived tissue or tumor tissue; (ii) contacting the obtained mRNA sample with a labelled probe of Brain Factor-1, under conditions permitting the probe to bind to mRNA encoding the Brain Factor;(iii) removing unbound probe from the sample;(iv) detecting the presence of bound, labelled-probe in the sample;(v) quantifying the amount of bound, labelled probe in the sample; and(vi) comparing the amount of bound, labelled probe in the sample to the amount of labelled probe which binds to a sample of non telencephalon-derived tissue or of telencephalon-derived tissue from an animal which expresses normal levels of the Brain Factor-1 in such tissue.

This invention provides an expression vector comprising the genomic DNA molecule of Brain Factor-1, Brain Factor-2 or Brain Factor-3 operably linked to a promoter.

This invention provides an expression vector comprising the cDNA molecule of Brain Factor-1, Brain Factor-2 or Brain Factor-3 operably linked to a promoter.

This invention also provides a host vector system comprising the above-described expression vectors in a suitable host cell. In an embodiment, the suitable host is a bacterial cell. In another embodiment, the suitable host is a eukaryotic cell.

This invention also provides a method of producing a Brain Factor which comprises growing the above-described host vector systems under conditions which permit transcription and translation, followed by recovering the protein so produced.

This invention also provides a purified, animal Brain Factor-1, a purified, animal Brain Factor-2 and a purified, animal Brain Factor-3. In an embodiment, the purified, animal Brain Factor is mammalian. In a further embodiment, the purified, mammlian Brain Factor is from mouse, rat or human.

This invention further provides a protein which comprises an amino acid sequence fused to the purified the above-described purified Brain Factor or to a fragment of the purified Brain Factor.

The above fusion protein may be generated by chemical or genetical engineering methods. For example, the DNA sequence encoding a Brain factor or a fragment of the Brain Factor can be ligated to another DNA molecules which encoding another protein of interest. Therefore, the ligated molecule will produce a fusion protein which have some or all of the Brain Factor protein.

This invention also provides a pharmaceutical composition comprising the above-described purified Brain Factor and a pharmaceutically acceptable carrier.

This invention provides a method of correcting an animal's defective synthesis of a Brain Factor which comprises administering to the patient an effective amount of the above pharmaceutical composition.

This invention provides a method of correcting an animal's defective synthesis of a Brain Factor which comprises: (i) isolating suitable cells from the animal; (ii) inserting the expression vector comprising the genomic or complementary DNA molecule of Brain Factor-1, Brain Factor-2 or Brain Factor-3 operably linked to a promoter into the cells under conditions permitting stable integration of the vector into the genome of the cells and expression of the DNA molecule; and (iii) reintroducing the cells into the animal from which they were isolated.

This invention also provides a method of correcting an animal's defective synthesis of a Brain Factor which comprises: (i) introducing the expression vector comprising the genomic or complementary DNA molecule of Brain Factor-1, Brain Factor-2 or Brain Factor-3 operably linked to a promoter into a neuroepithelial cell line under conditions permitting stable integration of the vector into the genome of the neuroepithelial cells; and (ii) administering the neuroepithelial cells to the animal under conditions permitting the cells to grow in the animal and synthesize the Brain Factor encoded by the expression vector.

This invention also provide an antibody which specifically recognizes the Brain Factor-1, Brain Factor-2 or Brain Factor-3. In an embodiment, the above antibody is monoclonal. This invention also provides a hybridoma cell which produces the monoclonal antibody which specifically recognizes the Brain Factor-1, Brain Factor-2 or Brain Factor-3.

As an example to produce polyclonal antibodies to BF-1, a 15 aa peptide corresponding to amino acids 161–174 plus a cysteine residue was synthesized, purified by HPLC and coupled to the carrier, keyhole limpet hemocyanin (KLH) and injected into rabbits with adjuvant at 4-week intervals. This peptide was chosen for its hydrophilicity and because it is not conserved between any of the known members of the gene family. Rabbits were sacrificed after four injections. Initial studies show this antisera reacts with BF-1 as tested by Western blot, using bactrially expressed BF-1 protein and immunoprecipitation of BF-1 protein translated in reticulocyte lysates (FIG. 16). This antisera can also immunoprecipitate BF-1 (FIG. 17).

This invention further provides a method of producing a monoclonal antibody which specifically recognizes a Brain Factor which comprises culturing the above-described hybridoma cell under conditions permitting antibody production, followed by recovering the antibody so produced. This invention also provide the above antibody labelled with a detectable marker.

This invention further provides a method of detecting the expression of a Brain Factor in an animal tissue which comprises:(i) isolating a sample of the animal tissue; (ii) contacting the sample with the above-described labelled antibody under conditions permitting the antibody to bind to the Brain Factor in the sample;(iii) removing unbound, labelled antibody from the sample; and (iv) detecting the presence of bound, labelled antibody in the sample, said presence indicating the presence of Brain Factor in the tissue.

This invention provides a method of detecting expression of a Brain Factor in a tumor comprises the steps of: (i) obtaining a sample of the tumor; (ii) contacting the sample with the above-described labelled antibody under conditions permitting the antibody to bind to the Brain Factor in the sample; (iii) removing unbound, labelled antibody from the sample; and (iv) detecting the presence of bound, labelled antibody in the sample, said presence indicating the presence of Brain Factor in the tumor.

This invention also provides a DNA vector which comprises the 5' nontranscribed region of the Brain Factor-1 gene, 3' nontranscribed region of the Brain Factor-1 gene and a gene of interest, linked operably.

This invention also provides a plasmid which comprises the above vector. In an embodiment, the plasmid is designated pTBL3. This plasmid, pTBL3, was deposited on Apr. 30, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pTBL3, was accorded ATCC Accession Number 75462.

This invention further provides a retroviral DNA vector which comprises the 5' nontranscribed region of the Brain Factor-1 gene, 3' nontranscribed region of the Brain Factor-1 gene and a gene of interest, linked operably.

This invention further provides the above-described retroviral vector, wherein the vector comprises DNA from a retrovirus corresponding to a 5' long terminal repeat, a 3' long terminal repeat, and a packaging signal.

This invention also provides plasmids which comprise the above-described retroviral vectors.

This invention provides an isolated, purified transcription factor expressed in the telencephalic region of the brain of a developing animal or in structures derived therefrom. For the purposes of this invention, an "isolated, purified" transcription factor is a nonnaturally occurring transcription factor, i.e., a transcription factor in a form which does not occur in nature. The term "transcription factor" as used herein means a protein whose presence is required to assist eucaryotic polymerases in starting RNA synthesis at correct sites on the DNA. The transcription factor may be a RNA polymerase II transcription factor, i.e., a factor which enables RNA polymerase II to start synthesis of mRNA at correct sites on the DNA. In one embodiment of this invention, the animal is a mammal, e.g., a mouse, rat or human.

The transcription factor of this invention is expressed in the telencephalon of the embryo of an animal and is also expressed, at a lower level, in the telencephalon-derived structures in the adult. The transcription factor of this invention is expressed in the cerebral hemispheres of the adult brian. The isolated, purified transcription factor provided by this invention may have the amino acid sequence shown in FIGS. 1 (Seq.I.D.Nos.1 and 2).

This invention also provides a protein which comprises an amino acid sequence fused to the isolated, purified transcription factor of claim 1 or to a fragment of the transcription factor. In one embodiment of this invention, the amino acid sequence is derived from glutathione transferase. In the presently preferred embodiment of this invention, the fragment of the transcription factor to which the amino acid sequence is fused corresponds to the DNA birding domain of the transcription factor.

This invention further provides a pharmaceutical composition comprising the transcription factor of this invention and a suitable carrier. Suitable carriers from a transcription factor are well known to those of ordinary skill in the art and include, but are not limited to, aqueous buffers. This invention still further provides a method of correcting an animal's defective synthesis of a transcription factor expressed in telencephalon-derived structures which comprises administering to the animal an effective amount of the pharmaceutical composition of this invention. "Correcting" an animal's defective synthesis of a transcription factor as used herein is intended to mean supplying the animal with an exogenous source of transcription factor when the animal itself synthesizes an insufficient amount of the transcription factor to meet its physiological needs. An "effective amount" of the pharmaceutical compositions is any amount of the composition effective to supply the animal with the transcription factor which the animal synthesizes in insufficient amounts. Methods of determining an effective amount are well known to those skilled in the art or can readily be determined by routine experimentation.

This invention provides an isolated nucleic acid molecule encoding the transcription factor of this invention. In one embodiment of this invention, the nucleic acid molecule is a messenger RNA molecule. In another embodiment of this invention, the nucleic acid molecule is a DNA molecule. The DNA molecule of this invention may be a cDNA molecule, e.g., a cDNA molecule having a nucleotide sequence substantially the same as the nucleotide sequence shown in FIG. 1 (Seq.I.D. No.1). The cDNA molecule may be labelled with a detectable marker, e.g., a radioisotope. The DNA molecule of this invention may also be a genomic DNA molecule.

Applicants have isolated a genomic DNA molecule which is approximately 20 kb in length and which includes all of the exons of the gene for the transcription factor. The genomic DNA molecule provided by this invention contains, in addition to the exons, DNA sequences which are involved with regulating the expression of the gene. These DNA sequences may be sequences to which factors bind that either promote or inhibit the expression of the gene. An example of such a factor is a transcription factor such as steroid hormone receptor. Accordingly, "correcting" an animal's defective synthesis of a transcription factor as used herein also means modulating the expression of the gene encoding the transcription factor. Such expression may be modulated by administering factors to the animal which either promote or inhibit expression of the gene. The ability of factors to promote or inhibit gene expression may be dependent on their ability to bind to DNA sequences which regulate gene expression. Such sequences involved in the regulation of the gene encoding the transcription factor of this invention are present in applicant's isolated genomic DNA molecule.

This invention provides a method of detecting the expression in the telencephalon-derived tissue of an animal of a transcription factor normally expressed in such tissue which comprises the steps of: isolating a sample of telencephalon-derived tissue from the animal; contacting the tissue sample with a labelled probe derived from the cDNA molecule of this invention under conditions permitting the probe to bind to mRNA encoding the transcription factor; removing unbound probe from the tissue sample; and detecting the presence of bound, labelled probe in the tissue sample, said presence indicating the expression of the transcription factor in the telencephalon-derived tissue. The animal may be a mammal, e.g., a mouse, rat or human. Methods of isolating telencephalon derive tissue from an animal are well known to those skilled in the art. Methods of contacting tissue samples with cDNA probes, conditions suitable for binding of cDNA probes to mRNA in a tissue sample and methods of removing unbound probe from a sample are also well known to those skilled in the art. Additionally, methods of detecting bound, labelled probe in a tissue sample are well known to those skilled in the art.

This invention also provides a method of diagnosing the abnormal expression of a transcription factor normally expressed in telencephalon-derived tissue which comprises the steps of: isolating a sample of tissue from the animal; contacting the tissue sample with a labelled probe derived from the cDNA molecule of this invention under conditions permitting the probe to bind to mRNA in the tissue sample; removing unbound probe from the sample; detecting the presence of bound, labelled probe in the sample; quantifying the amount of bound, labelled probe in the sample; and comparing the amount of bound, labelled probe in the sample to the amount of labelled probe which binds to a sample of non telencephalon-derived tissue or to a sample of telencephalon-derived tissue from a subject which expresses normal levels of the transcription factor in such tissue. Methods of isolating sample of telencephalon-derived tissue, of contacting such tissue with a labelled probe under conditions permitting binding of the probe to mRNA in the sample and of removing unbound probe from the sample are well known to those skilled in the art or can readily be determined by routine experimentation. Methods of detecting and quantifying the amount of bound, labelled probe in a sample are also well known to those skilled in the art. The transcription factor of this invention is not normally expressed in non telencephalon-derived tissue.

Identification of the transcription factor in such tissue is indicative of abnormal gene expression in the tissue. Comparison of the amount of bound, labelled probe in a sample of telencephalon-derived tissue from a subject animal with a similar sample from a normal animal will indicate whether the subject animal expresses an abnormal amount of the transcription factor of this invention. The presence of abnormal amounts of the transcription factor of this invention is related to the presence of an abnormal developmental state in the cells of telencephalon-derived tissue in which the transcription factor is expressed. The method provided by this invention is therefore useful in diagnosing the existence of an abnormal developmental state in the telencephalon derived tissue of an animal. Such animals include, but are not limited to mammals, e.g., mice, rats or humans.

This invention provides an expression vector comprising the isolated DNA molecule of this invention operably linked to a RNA polymerase promoter. Examples of such expression vectors include, but are not limited to, plasmids, viruses, cosmids or phages.

This invention provides a method of correcting an animal's defective synthesis of a transcription factor expressed in telencephalon-derived structures which comprises the steps of: isolating suitable cells from the animal; inserting the expression vector of this invention into the cells under conditions permitting stable integration of the vector into the genome of the cells and expression of the DNA molecule; and reintroducing the cells into the animal from which they were isolated. Cells suitable for use in accordance with the practice of this invention are well known to those skilled in the art or can readily be determined by routine experimentation. Methods of isolating such cells, and of readministering the cells to the animal, are also well known to those skilled in the art. "Inserting" an expression vectors as used herein is intended to mean any commonly accepted method of introducing an expression vector into cells such that the vector will stably integrate into the genome of the cell in a manner permitting the expression of the isolated DNA molecule in the integrated vector. Examples of such methods include, but are not limited to, calcium phosphate precipitation, electroporation or microinjection.

This invention also provides a method of correcting an animal's defective synthesis of a transcription factor expressed in telencephalon-derived structures which comprises the steps of: introducing the expression vector of this invention into a neuroepithelial cell line under conditions permitting stable integration of the vector into the genome of the neuroepithelial cells; and administering the neuroepithelial cells to the animal under conditions permitting the cells to grow in the animal and synthesize the transcription factor encoded by the expression vector. "Introducing" a vector into a cell in accordance with the practice of this invention is intended to mean any commonly accepted practice of introducing an expression vector into cells such that the vector will stably integrate into the genome of the cell in a manner permitting the expression of the isolated DNA molecule in the integrated vector. Examples of such methods include, but are not limited to, calcium phosphate precipitation, electroporation or microinjection. Neuroepithelial cells useful in accordance with the practice of this invention will be cells which can be administered to the animal without being rejected by the animal's immune system. Identification of such cells is within the purview of one of ordinary skill in the art. Methods of administering such cells are also well known to those skilled in the art.

This invention provides a host vector system comprising the expression vector of this invention in a suitable host cell. In one embodiment of this invention, the suitable host cell is a bacterial cell. In another embodiment of this invention, the suitable host cell is a eucaryotoic cell.

This invention also provides a method of producing a transcription factor expressed in the telencephalic region of the brian of a developing vertebrate animal or in structures derived therefrom, which comprises growing the host vector system of this invention under conditions which permit transcription and translation, followed by recovering the protein so produced. Conditions permitting transcription and translation in a host vector system are well known to one of ordinary skill in the art or can readily be determined by routine experimentation. Methods of recovering proteins expressed by a host vector system are also well known to those skilled in the art.

This invention provides an antibody which specifically recognizes the transcription factor of this invention. The antibody may be labelled with a detectable marker. In one embodiment of this invention, the antibody is a monoclonal antibody. This invention also provides a hybridoma cell which produces the monoclonal antibody of this invention. This invention further provides a method of producing a monoclonal antibody which specifically recognizes a transcription factor expressed in the telencephalic region of the brain of a developing animal or in structures derived therefrom which comprises culturing the hybridoma cell of this invention under conditions permitting antibody production, followed by recovering the antibody so produced. Methods of culturing hybridomas to produce monoclonal antibodies and of recovering monoclonal antibodies produced by hybridomas are also well known to those skilled in the art or can readily be determined by routine experimentation.

This invention provides a pharmaceutical composition comprising the antibody of this invention and a suitable carrier. Suitable carriers are well known to those of skill in the art or can readily be determined by hem without undue experimentation. Examples of suitable carriers include, but are not limited to, aqueous buffers. This invention also provides a method of detecting the presence in an animal of a transcription factor normally expressed in the telencephalic region of the brain of a developing animal or in structures derived therefrom which comprises the steps of: isolating a sample of suitable tissue from the animal; contacting the sample with the pharmaceutical composition of this invention, wherein the antibody is labelled with a detectable marker, under conditions permitting the antibody to bind to transcription factor in the sample; removing unbound, labelled antibody from the sample; and detecting the presence of bound antibody in the sample, said presence indicating the presence of transcription factor in the tissue sample. Methods of isolating telencephalon-derived tissue from an animal, of contacting the tissue with a pharmaceutical composition comprising a labelled antibody under conditions permitting binding of the antibody to protein in the sample and of removing unbound antibody from the sample and of detecting bound, labelled antibody in the sample are well known to those skilled in the art or can readily be determined by them without undue experimentation.

This invention also provides a method of detecting the presence in a patient of tumors arising from telencephalic-derived tissue which comprises the steps of: (i)isolating a sample of tumor tissue from the patient; contacting the sample with an effective amount of the pharmaceutical composition of claim 30, wherein the antibody is labelled with a detectable marker, under conditions permitting the antibody to bind to transcription factor in the sample; removing unbound, labelled antibody from the sample; and detecting the presence of bound, labelled antibody in the sample, said presence indicating the presence of transcription factor and thereby the presence of a tumor arising from telencephalic-derived tissue. Methods of isolating tumor tissue from an animal, of contacting the tissue with a pharmaceutical composition comprising a labelled antibody under conditions permitting binding of the antibody to protein in the sample and of removing unbound antibody from the sample and of detecting bound, labelled antibody in the sample are well known to those skilled in the art or can readily be determined by them without undue experimentation.

This invention will be better understood from the Examples which follow. However, those skilled in the art will readily appreciate that the specific examples detailed are only illustrative of the invention as described more fully in the claims which follow thereafter.

First Series of Experiments

Results

Isolation of cDNA clones for BP-1

Figure 2:
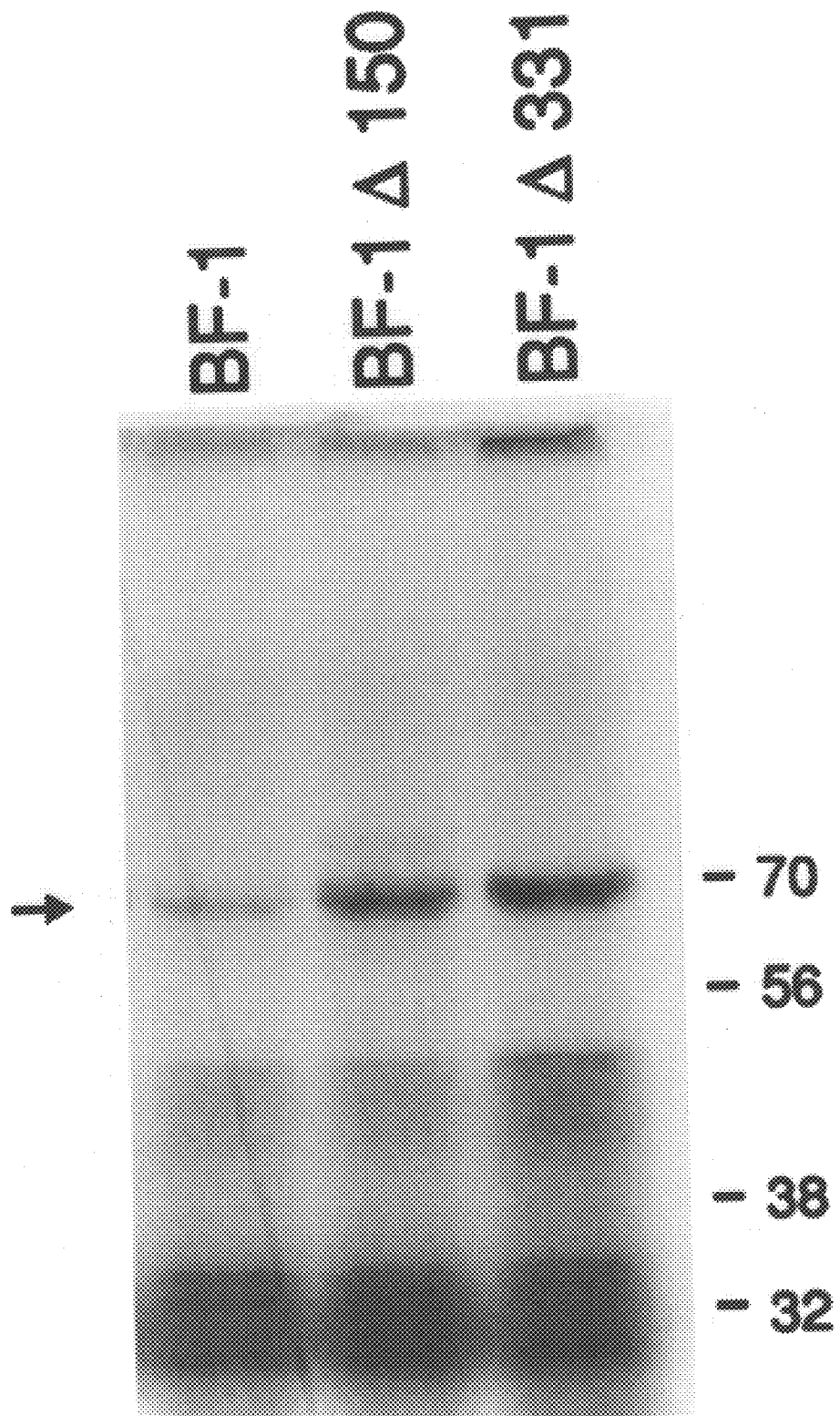
FIG. 2 Translation of the BF-1 protein in reticulocyte lysates from transcripts synthesized in vitro from the full length BF-1 template (lane 1), or templates deleting the 5' end of the cDNA 150 bp, BF-1Δ150 (lane 2) or 331 bp, BF-1Δ331 (lane 3). The size of the major product is the same for all three, demonstrating that the initiation site lies downstream of nucleotide 331. The lower MW products represent internal initiations, while the minor higher MW product present with templates BF-1 and BF-1Δ150 represents initiation at an upstream GUG at nucleotide 254. As expected, this higher MW product is absent with template BF-1Δ331. These additional products are attributable to the more permissive initiations which occur in reticulocyte lysates.

We knew that Drosophila fork head or a closely related protein is expressed in the central nervous system of Drosophila (Weigel, Jurgens et al. 1989) while the three HNF-3 proteins were not expressed in the mammalian brain (Lai, Prezioso et al. 1991). Therefore we postulated that additional members of the HNF-3 gene family, which were critical to the development of the central nervous system, would be expressed in the mammalian brian. Northern analysis using an HNF-3a probe which spanned the DNA binding domain, was performed at low stringency. This revealed a 2.9 kb RNA species from whole brain tissue which was no longer detected after a high stringency wash. This probe was then used to screen a rat whole brain lambda gt11 DNA library. From a screen of 500,000 recombinants, 10 positive clones were obtained of which 6 proved to be from the same cDNA as assessed by restriction and partial sequence analysis. One clone was 2.9 kb in length and contained an open reading frame (FIGS. 1A–1C) which encodes a protein of 480 amino acids, which we call BF-1 (brain factor-1). The ATG at 443 is the translation initiation start site. It is the first to have a purine at the -3 position (Kozak 1986), is preceded by an in-frame termination codon and deletions of up to 331 nucleotides of the 5' end of the cDNA do not alter the size of the protein translated in reticulocyte lysates from RNA transcribed in vitro using T7 or T3 RNA polymerase compared to that translated from the full length cDNA (FIG. 2). The translated protein of 480 amino acids migrates with an apparent molecular weight on SDS-polyacrylamide gels of 67,000 daltons. For comparison, the translated HNF-3a protein of 466 amino acids migrates with an apparent size of 60,000 daltons. This size is different than previously reported (Lai et al. 1990) because the pre-stained molecular weight markers we have been using were recently recalibrated by the manufacturer (Sigma) to be larger than previously indicated. Both proteins migrate on SDS-gels more slowly than expected from the calculated size.

Expression of BF-1 is distinct from that of HNF-3α, 3β and 3γ

Figure 3:
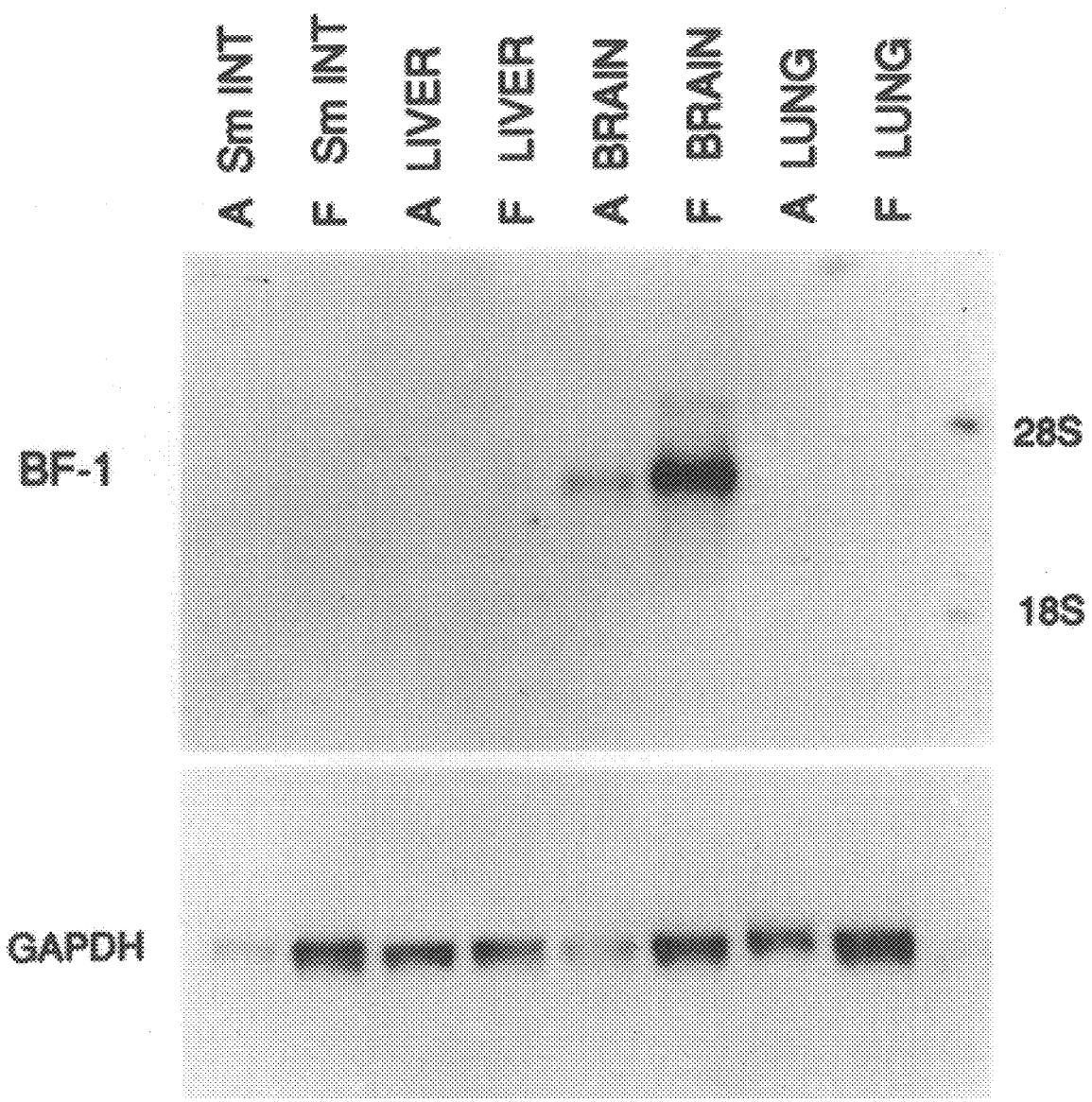
FIG. 3 Northern analysis of poly A+ RNA from adult (A) and E17 fetal (F) rat tissues. One major mRNA species is detected in the brain at 2.9 kB, with a probe for BF-1. A minor band is seen at 5 kB. This mRNA is not detected in the other tissues even with prolonged exposure of the blot. The same blot was reprobed with GAPDH to assess the quantity of RNA. Sm INT—small intestine.
Figure 4A:
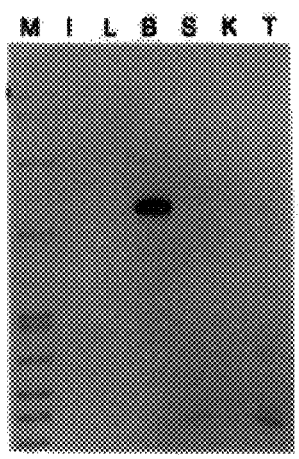
FIGS. 4A and B Ribonuclease protection assays of total RNA from rat tissues. A 309 nucleotide fragment is specifically protected by the BF-1 mRNA. A) The protected band is detectable only in the brain. M—molecular weight markers; I—small intestine; L—liver; B—brain; S—spleen, K—kidney; T—testis. B) RNA prepared from different regions of the adult brain, adrenal gland, and whole brain or liver from four different stages of development. CAUD— caudate putamen; Fr CORT—frontal cortex; Oc CORT—occipital cortex; CEREB—cerebellum; OLF—olfactory bulb; HIPP—hippocampus; THAL—thalamus; Ad—adult; NB—newborn; E17-embryonic day 17; E14-embryonic day 14; BR-brain; LIV-liver.

We examined the expression pattern of BF-1 initially by Northern analysis of poly A+ RNA isolated from both adult and fetal rat tissues. FIG. 3 shows that a 2.9 kB mRNA species is present in samples isolated from total brain using a probe derived from the BF-1 cDNA which does not contain the DNA binding domain. No expression is apparent in the lung, liver, and intestine (FIG. 3). The quantity of RNA in each lane is assessed by hybridization of the filter with a probe for GAPDH, which is found in similar abundance in all tissues. The Northern analysis was confirmed with RNase protection assays using a probe corresponding to nucleotides 1140–1449 of the cDNA. FIG. 4A shows the presence of the specifically protected probe of 309 nucleotides with total RNA from brain but not from liver, kidney, spleen and intestine. The quantity of the RNA was assessed to be equivalent among all the samples used in these assays by staining after electrophoresis in an agarose gel to visualize the 18S and 28S mRNA bands.

Levels of expression of BF-1 in the developing rat brain

Figure 4B:
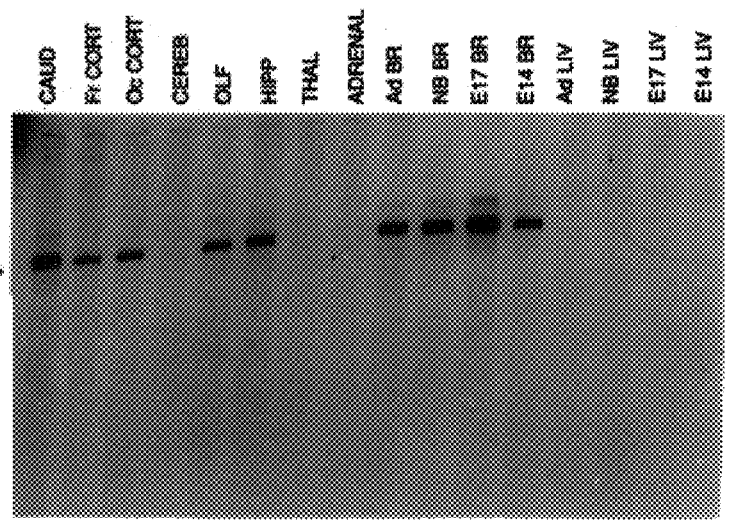

Northern analysis showed that the mRNA was several-fold more abundant in embryonic day 17 (E17) brain than in the adult brain (FIG. 3). Additional studies which allowed better quantitation were performed with RNase protection assays on RNA from tissues during fetal development. FIG. 4 shows that BP-1 expression is detectable in E14 brain, increases to peak levels by day 17 and declines thereafter to adult levels. The data show that BF-1 is four-fold more abundant in E17 brain compared to the adult brain. Fetal and adult liver RNA were also assayed and not found to express BF-1 at any stage of development. We used total RNA isolated from dissected regions of the adult rat brain to study the regional distribution of BF-1 expression in RNAse protection assays. FIG. 4B reveals that BF-1 is expressed in the cortex, olfactory bulb, hippocampus and in the caudate putamen. Expression is absent in the cerebellum and thalamus. Adrenal tissue also does not express BF-1. The amount of RNA in each sample was verified to be the same in a Northern blot using a probe to 18S RNA (Ehrlich et al. 1990).

Expression of IF-1 is restricted to the telencephalon of the developing brain

Examination of rat brain sections by in situ hybridization, confirmed the region restricted expression pattern of BF-1. FIGS. 5J and 5K are autoradiographs of sections of adult brain hybridized with an antisense probe for BF-1. The cerebral cortex, caudate putamen, hippocampus and dentate gyrus show levels of BF-1 expression significantly above background while the thalamus, cerebellum and brainstem do not. This restricted expression to telencephalon-derived structures is even more clearly seen in the E17 brain. FIG. 5E shows a brightfield view of a parasagittal brain section. The autoradiograph of this section (FIG. 5F) and two coronal sections (FIGS. 5G and H) shows high level expression in the cerebral cortex and caudate putamen and no significant expression in the more caudal regions of the brain. The specificity of this signal for BF-1 is shown in FIG. 5I, an autoradiograph of a section parallel to that shown in 5E, hybridized with a sense probe to BF-1. This restriction of BF-1 expression is established early in development. FIGS. 5A–D show that BF-1 expression is limited in the nervous system to the most rostral region of the developing brain. We detect high levels of BF-1 MRNA in the ventricular zone surrounding the lateral ventricles at E11.5 soon after the telencephalic evaginations arise (Rugh 1968). The level of expression declines between E17 and the adult (FIGS. 5J,K), consistent with the results obtained with analysis of whole brain RNA. The autoradiographs for the embryonic sections are exposed for one-third of the time as the adult sections. Thus expression levels per cell falls about 10–20 fold.

Figure 5B:
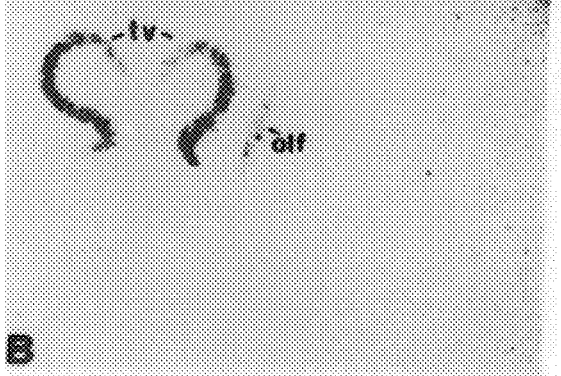
Figure 5C:
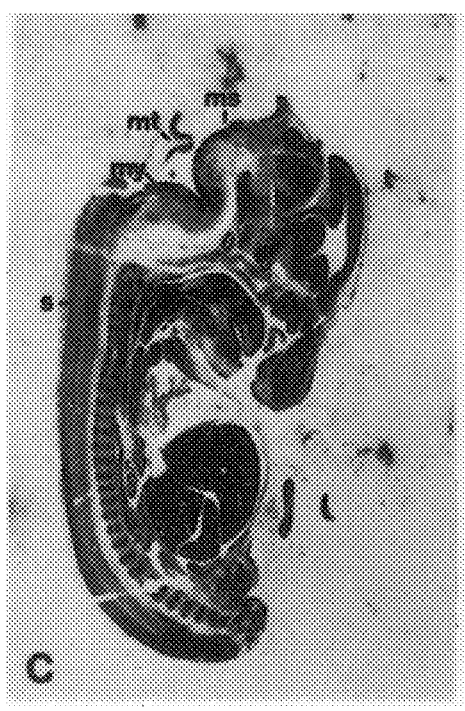
Figure 5D:
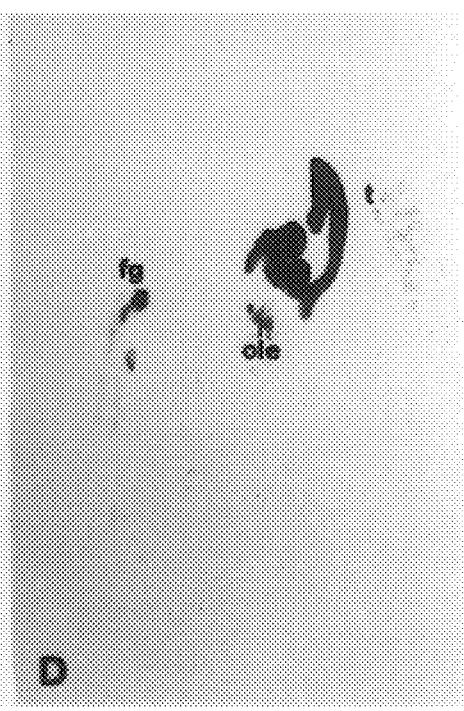

Higher magnification views show more clearly the restriction of expression within the developing forebrain to the telencephalon. High levels of BF-1 are detectable in the rostral neuroepithelium of E10 embryos, shown in matching brightfield and darkfield views (FIGS. 6A–6D). At this stage, it is difficult to distinguish the border between the telencephalic and diencephalic neuroepithelium. The rapid proliferation of the cells of the telencephalon results in distinct telencephalic vesicles by E11.5 (FIG. 6C). Here we obverse high levels of BF-1 expression in the neuroepithelium surrounding the lateral ventricles. By contrast, structures of the diencephalic neuroepithelium, including the optic stalk and the optic cup which will develop into the retina, are clearly devoid of BF-1 (FIGS. 6C, 5A, 5B). In order to further demonstrate the restriction of BF-1 expression to the telencephalic neuroepithelium and the structures arising from it, we show two additional views of the telencephalon and diencephalon from E13.5 in FIG. 7. At this stage, the earlier onset of neurogenesis in the basal telencephalon is apparent by the presence of larger differentiating fields around the basal telencephalic neuroepithelium, compared with the cerebral cortical neuroepithelium (FIGS. 7A and 7B). The differentiating cells of the basal telencephalon express BF-1 at least as highly as the neuroepithelium. Expression of BF-1 abruptly terminates caudal to this region. An adjacent section further shows the absence of expression in the diencephalon and also shows absence of expression in the medial wall of the telencephalic vesicles (FIGS. 7C and 7D). This region of the telencephalic neuroepithelium expresses BF-1 earlier in development but begins to decrease expression with the infolding of the superior bridge and the establishment of the telencephalic vesicles (FIGS. 6E and 6F).

Figure 6D:
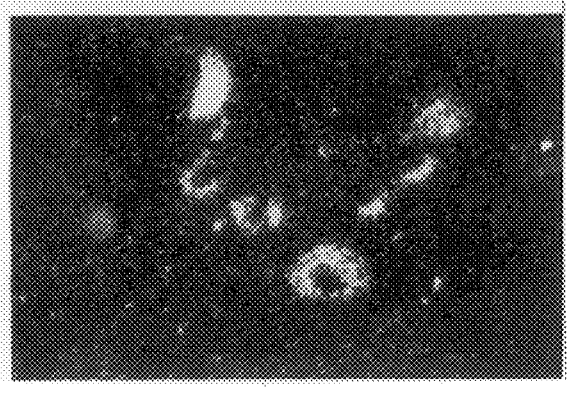
Figure 6E:
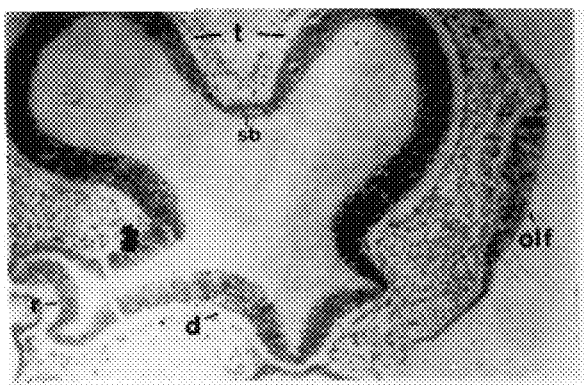
Figure 6F:
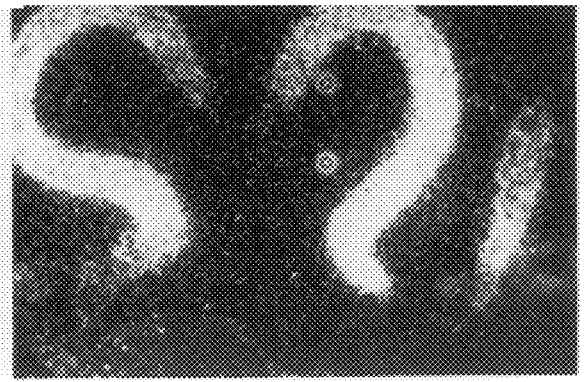

A few localized sites of expression are detected outside of the central nervous system, including the olfactory placode which gives rise to the nasal epithelium (FIG. 6C), the auditory vesicle and the pharyngeal pouches (FIGS. 6C and 6D). Expression at these sites declines through embryogenesis. The absence of expression through development in the tissues where HNF-3 proteins are expressed, the liver, the lung and the intestine are confirmed by in-situ data (FIGS. 5A–D).

BF-1 shares homology with the HNF-3 family in the DNA binding domain

Comparison of the sequence of BF-1 with the members of the HNF-3 family shows that it contains a homologous region from amino acids 162–271 corresponding to the DNA binding domain previously identified in the HNF-3 family (FIGS. 1A–1C). However, whereas the HNF-3 family members are 85% identical within this entire 110 amino acid region, BF-1 is considerably more divergent. This divergence is greater than that of the Drosophila fork head gene from the rat HNF-3 genes. Thus, fork head is the Drosophila homolog of HNF-3α, 3β and 3γ, while BF-1 is in a distinct subfamily. The homology is not uniform within this domain. It is apparent that the central portion with 74% of the amino acids (32/43 aa) identical comprises the most highly conserved structure while the carboxyl third of this region is only 36% identical (13/36 aa). FIG. 1 shows the amino acids in the DNA binding domain which are identical to at least two of the other four members of the HNF-3/fork head family. These differences raised the likelihood that BF-1, if it bound to DNA, might have a distinct binding specificity. The sequence of BF-1 is notable for several other features. First, it does not share the two other conserved short domains II and III carboxyl to the binding domain which are found in the HNF-3 and fork head genes (Lai, Prezioso et al. 1991). However, a short sequence similar to that in domain II is present in the amino terminal end of BF-1 (amino acids 18–24, FIG. 1). The function of these domains remains unknown. Finally, BF-1 contains proline and glutamine rich regions, which have previously been shown in other transcription factors to confer activation function (Courey and Tjian 1988; Mermod et al. 1989).

BF-1 is a sequence specific DNA binding protein with a distinct binding specificity Because of the differences in the amino acid sequence in the binding domain as compared with HNF-3 proteins, we were not surprised to find that BF-1 did not bind readily to the strong HNF-3 site from the transthyretin (TTR) promoter. This site has been previously shown to be located between nucleotides -85 and -111, upstream of the transcription initiation site (Costa et al. 1989). However, when we used a large amount of bacterially expressed fusion protein (25 ng) which contained the binding domain of BF-1, we were able to detect a weak complex in gel mobility shift experiments using this probe. This suggested that BF-1 was a DNA binding protein with a low affinity for this site. We reasoned that a preferred binding site would have some similarity to the site in the TTR promoter, so we obtained and tested a series of oligonucleotides which contained different sites which bind to the HNF-3 proteins. We compared two bacterially produced fusion proteins containing 206 amino acids of the BF-1 protein in gel mobility shift assays with HNF-3 proteins from a liver extract. Interestingly, we found one HNF-3 site from the promoter of the HNF-1a gene called B2 (Kuo et al. 1992) which binds to BF-1 with at least twenty-fold greater affinity than any of four other sites tested. FIG. 8 shows a gel mobility shift experiment using two different probes, the TTR promoter site and the B2 site. Whereas liver nuclear extract (containing at least three HNF-3 proteins) binds to the TTR site with a slightly higher affinity compared to the B2 site, both BF-1 fusion proteins have a markedly greater affinity for the B2 site compared to the TTR site. One fusion protein using the pET vector adds 14 aa to the amino terminal end (Rosenberg et al. 1987) while the other using the pGEX vector adds 27.5 kD of glutathione tranferase to the amino terminal end (Smith and Johnson 1988). These 206 amino acids of BF-1 contain the entire DNA binding domain as determined by sequence homology with the HNF-3 proteins. It has been determined for HNF-3 proteins that the binding domain alone has DNA binding properties indistinguishable from the intact protein (Tao and Lai, unpublished data). BF-1 also did not bind to three other HFN-3 sites from the α-1 antitrypsin gene, a second site from the transthyretin gene (Costa, Grayson et al. 1989), and the albumin gene (Liu et al. 1991). These results show that BF-1 has a distinct DNA binding specificity from that of the HNF-3 proteins. The identical DNA binding properties of two different BF-1 fusion proteins indicate that DNA binding is attributable to the BF-1 portion of the protein. However, the affinity of BF-1 for the B2 site is relatively low compared to the affinity of the HNF-3 proteins for this site. Studies are in progress to identify the optimal recognition sequences for this protein.

Discussion

We have cloned and characterized, BF-1, a new member of the HNF-3 family from a rat brain cDNA library. BF-1 shares homology in the DNA binding domain with HNF-3α, 3β, 3γ and Fork head but clearly belongs to a different subfamily based on significant divergence in the carboxyl third of this domain. This divergence in sequence likely reflects some differences in function as underscored by our findings that BF-1 is expressed in a completely distinct pattern than the HNF-3 proteins and that BF-1 has a different DNA binding specificity. Consistent with a role in central nervous system development, BF-1 is expressed at high levels in specific regions of the brain during embryogenesis. These results suggest that an extended family of transcription factors related to the HNF-3 proteins exists which have a boarder role in mammalian development than previously believed. Members of the extended HNF-3 family are not only expressed in gut endoderm derived tissues but in the central nervous system as well. The emerging picture is that of a large gene gamily with distinct subfamilies of transcription factors, each of which may regulate the development of distinct subsets of tissues. The brain-specific subfamily comprises BF-1 and at least two additional members. An additional member of this family which is present in lymphoid cells has recently been reported (Li et al. 1991).

The restricted expression of BF-1 to the telencephalon at early stages in brain development suggests that it plays a role in the regional differentiation of the neural tube. It has been suggested that signals from the underlying mesoderm during gastrulation lead to the commitment of different regions of the neural tube to form different parts of the central nervous system. The forebrain forms above the prechordal plate (Bergquist and Kallen 1954), rather than the notochord and floor plate which has been shown to provide inductive signals to the spinal cord (Placzek, Tessier-Lavigne et al. 1990; Yamada et al. 1991). Thus, it would be expected that different signals are received in this region of the neural tube, resulting in distinct patterns of gene expression. The forebrain subsequently subdivides into the telencephalon and the diencephalon. The restricted expression of BF-1 to the rostral portion of the forebrain prior to its morphologically apparent subdivision into two vesicles and its structural homology to fork head, a putative transcriptional regulator, suggests that it is likely to be an important intermediary in the regulatory cascade which commits the cells of the rostral neural tube to the formation of the telencephalon. The fork head mutation causes a homeotic transformation of the terminal regions of the embryo. Foregut and hindgut are replaced by ectopic head structures (Jurgens and Weigel 1988). BF-1 expression is first evident in the proliferating neuroepithelial precursor cells surrounding the telocoel. As development progresses, these cells differentiate into neuronal and glial cells and migrate outward. The expression of BF-1 persists in the post-mitotic cells and by E17 is uniformly detected in the telencephalic structures.

Expression is clearly evident in neurons as exemplified by the in-situ signals of the hippocampus and dentate gyrus (FIG. 5K). Expression in the adult is restricted to the gray matter and the large increase in BF-1 expression between E14 and E17 correlates well with the period of rapid neuronal proliferation. Furthermore, expression of BF-1 per cell in the cerebral hemispheres declines postnatally, correlating with the major period of glial proliferation. These results suggest that BF-1 is primarily expressed in neurons but we cannot exclude expression in glia. The relative uniformity of expression in the cerebral cortex and the caudate putamen indicates that BF-1 does not primarily direct the final differentiation of the many neuronal phenotypes found in these parts of the brain. Rather, BF-1 appears to function at an earlier step in the differentiation pathway to commit the precursor cells to form specific regions of the brain and not specific cell types. Its restriction to the rostral end of the neural tube is reminiscent of the restriction of fork head to the anterior and posterior termini of the early Drosophila embryo. Thus we postulate that BF-1 functions in regional specialization of the central nervous system in a manner analogous to the function of fork head in the regional specialization of the terminal structures in Drosophila.

Other putative transcriptional regulators have been found to be restricted to specific regions of the developing brian, including several homeodomain proteins and one zinc finger protein in specific rhombomeres of the hindbrain (Murphy, Davidson et al. 1989; Wilkinson, Bhatt et al. 1989; Wilkinson, Bhatt et al. 1989; Kessel and Gruss 1990; He and Rosenfeld 1991). Only a few examples of region-specific expression exists for the other regions of the brain. En-2 is expressed at the midbrain and hindbrain junction(Davis and Joyner 1988; Davis et al. 1988) and recently, two genes related to Distal-less were found to be expressed in a restricted pattern within the forebrain. Tes-1 and Dlx are expressed in the ventral forebrain of the mid-gestation embryo, in both the telencephalon and diencephalon (Porteus et al. 1991; Price et al. 1991). These factors along with BF-1 are likely to be part of the molecular basis of the regional organization of the developing neural tube. Still other transcription factors such as several members of the POU-domain family which are expressed in specific patterns in the developing brain but are not restricted to any single region (He et al. 1989), may function to determine specific phenotypes such as the different types of neurons and glia. The function of BF-1 in the adult brain is not readily apparent but may be related to maintaining the expression of those genes which are common to telecephalon derived structures. The product of one such gene has been detected as a telencephalon specific antigen in the rabbit (Mori et al. 1987) This antigen is restricted to the gray matter of the cerebral hemispheres and increases postnatally from low levels at birth.

Experimental Procedures:

Isolation and sequencing of cDNA clones of rat and murine BF-1

The rat BF-1 cDNA was obtained by screening a lgt11 library from whole adult rat brain generously provided by Dr. Streamsen Chua, using a random hexamer primed probe spanning nucleotides 596–923 of the HNF-3α cDNA. This probe contains the region encoding the DNA binding domain. Hybridization and washes were performed as previously described except for hybridization at 50° C. and the final wash at 50° C. in 2× SSPE. From 500,000 recombinants, 10 positive clones were analyzed further. Six of these proved to be overlapping clones of a single cDNA as determined by restriction mapping and partial sequence. The largest clone was used for subsequent studies.

Sequencing was performed by the dideoxy chain termination method on double stranded templates. The sequence was determined completely on both strands with overlapping subcloned and exonuclease shortened templates, and for nucleotides 1–2000 also with ITP-containing sequencing mixes (United States Biochemicals Sequenase kit) to eliminate compression artifacts.

Northern and ribonuclease protection analyses

RNA was isolated from rat tissues by the acid guanidinium thiocyanate-phenol-chloroform extraction method (Chomczynski and Sacchi 1987; Puissant and Houdebine 1990). Pregnant Sprague-Dawley rats were obtained from Harlan Sprague Dawley, timed at embryonic day 0.5 on the morning following an evening mating. Poly(A)+RNA was selected by chromatography on oligo(dT) cellulose. Northern analyses with 2 mg poly-A+ RNA were performed as previously described.

Ribonuclease protection assays were performed with 10 mg total RNA as described previously (Costa et al. 1986).

RNA probes were synthesized from a pBluescript plasmid containing the fragment of the BF-1 cDNA from nucleotides 1140–1149, linearized with PvuII, using T7 polymerase. The probe is 457 nucleotides in length and the protected fragment is 309 nucleotides. Samples were analyzed on 6% acrylamide-urea gels which were dried and exposed to X-ray film with screens for 16–48 hrs.

In-situ hybridization

Brain tissue was obtained from adult male Sprague-Dawley rats perfused with 4% paraformaldehyde or rat embryos. 8 micron paraffin sections were dewaxed in xylene and then processed essentially as described previously (Kuo et al. 1988). S-35 labeled riboprobes were synthesized using T7 (antisense) or T3 (sense) RNA polymerase from linearized plasmid templates containing the BF-1 cDNA from the Nhe I site at nucleotide 1265 to the 3' end. This probe does not contain the sequence encoding the DNA binding domain. Hybridization was for 16 hrs at 58° C. and the high stringency washes were performed at 60° C. in 2× SSC/50% formamide. Embryonic tissue sections were exposed to film for 16 hrs and to NTB-2 emulsion for 48 hrs. Adult sections were exposed for 48 hrs and 6 days respectively.

Fusion proteins and gel mobility shift assays

The fragment of the rat BF-1 cDNA from nucleotides 785 to 2240 was cloned into the BamHI site of the pGEX-3X vector (Pharmacia®) which yields a protein with 27.5K of glutathione transferase fused to 206 amino acids of BF-1 containing the DNA binding domain. The protein was expressed in *E. coli* SF8 cells. The fusion protein was purified from the crude bacterial extract by adsorption to glutathione agarose beads followed by elution with glutathione (Smith and Johnson 1988). The quantity of the partially purified protein used in binding assays was determined by Coomassie Blue staining. A second expression plasmid was constructed by ligating this fragment of BF-1 into the BamHI site of the pET-3c vector which yields a protein of 14 amino acids fused to 206 amino acids of BF-1. The crude lysate from bacteria expressing this fusion protein were used directly in binding assays (Studier and Moffatt 1986). 5 μg of BF-1 pET bacterial lysate, 25 ng of BF-1 pGEX, or 5 μg of liver nuclear extract was incubated with either B2 or TTR oligonucleotide probe as described previously (Lai, Prezioso et al. 1990).

The sequence of the binding site oligonucleotide from the transthyretin (TTR) promoter and the gel mobility shift assay have been described previously. The sequence of the binding site oligonucleotide from the HNF-1 promoter (B2) has also been described (Kuo, Conley et al. 1992).

Second Series of Experiments

Cloning of BF-1 cDNA into plasmid pBluescript KS

Lambda phage carrying the rat BF-1 cDNA was purified and the phage DNA was isolated by standard methods.

cDNA in lambda gt11 vector was excised with restriction enzymes EcoRI and NotI and cloned into the plasmid vector pBluescript KS.

This cDNA were cloned into EcoRI and NotI sites of pBluescript KS plasmid vector and can be excised using these restriction enzymes (FIG. 12). The plasmid made is designated, pBSKS-BF-1.

Mouse BF-1 cDNA

Several cDNA from a new born mouse brain lambda ZAPII library (purchased from Stratagene) was isolated using a probe from the rat BF-1 cDNA. Plasmid containing the cDNA were excised from the lambda phage according to the protocols of Stratagene. These plasmids contain the cDNA was EcoRI and XhoI fragments. Three distinct cDNA were identified based on sequence comparison. One is completely homologous to the rat cDNA and is >98% identical (mN13). A second cDNA is homologous except at the 5' end which diverges completely (mN3). A third has a deletion in the 3' untranslated region (mN11). These three cDNA arise from the alternative splicing of transcripts from one gene.

Genomic DNA for BF-1

The rat cDNA for BF-1 was used as a probe to screen and isolate a lambda phage clone containing the mouse genomic DNA for BF-1. The vector is lambda Gem 12 (Promega) and the insert can be excised with several restriction enzymes including BamHI. A clone was identified which contains an approximately 15 kB piece of genomic DNA which includes the entire sequence encoding the BF-1 protein, as well as approximately 10 kB of 5' flanking sequence. The 3' end of the clone is not yet fully mapped, but contains the 3' flanking sequence. These flanking sequences contain the regulatory elements which control the expression of BF-1 in a cell-specific manner. We have identified the transcription start sites for BF-1. There are two major sites and several minor sites. A restriction map of the genomic DNA is shown in FIG. 9 with the positions of the major start sites. The two major start sites leads to the two distinct cDNA which are divergent at the 5' end (mN3 and mN13). The protein translated from these two cDNA are identical.

Generation of a vector useful to express protein of interest in a cell-specific manner The nontranscribed regions of the BF-1 gene was further studied.

Approximately 10 kilobase of the 5' end of the nontranscribed region and about 3 kilobase of the 3' end of the nontranscribed region of the BF-1 gene are subcloned in a plasmid, called pTBL3. A lacZ gene was inserted between the 5' and 3' regions to confirm and define the regulatory regions which are necessary to define the expression pattern of this gene. Using this plasmid, transgenic mouse is made.

Map of the Bf-1-lacZ expression cassette in plasmid pTBL3. SfiI and XhoI linkers were introduced into the SphI and EcoRI sites of the vector, pGEM4 respectively. Then whole BF-1-lacZ expression cassette was cloned into the SfiI and XhoI sites of the modified vector. NcoI and KpnI are not unique sites.

Generation of transgenic mice

The linearized DNA fragment containing the BF-1 gene and lacZ sequence was purified and injected into mouse eggs. These eggs are then reimplanted into the reproductive tract of female mice and allowed to develop to term according to standard protocols.

The lacZ expression in the transgenic animal reflects the expression pattern regulated by the BF-1 gene. Expression is monitored by staining the tissues from the animal in a solution which yields a blue color in the cells which express β-galactosidase activity encoded by lacZ. One line of mice we have generated demonstrates restriction of lac Z expression to the telencephalic structures of the brain.

Analysis of the transgenic mouse generated indicates the lac-z gene is now expressing in the cell which expresses the BF-1 gene. This result show that the non transcribing regions is useful to direct expression of a protein of interest in a cell-specific manner in the brain.

Third Series of Experiments

Molecular cloning of BF-2 (Brain Factor-2) and BF-3 (Brain Factor-3)

Rat BF-2 and BF-3 partial cDNA Using the HNF-3a cDNA probe used for isolating BF-1 cDNA, we also isolated two additional cDNA which are distinct but related to BF-1 by sequence homology. These cDNA were isolated from lambda gt11 with inserts cloned into EcoRI and NotI sites. These cDNA contain only part of the protein coding sequence for these two proteins. These cDNA were cloned into EcoRI and NotI sites of pBluescript KS.

The rat BF-2 cDNA was cloned into EcoRI and NotI sites of pBluescript KS plasmid vector and can be excised using these restriction enzymes. The plasmid made is designated, pBSKS-BF-2.

The rat BF-3 cDNA was cloned into EcoRI and NotI sites of pBluescript KS plasmid vector and can be excised using these restriction enzymes. The plasmid made is designated, BF-3.

Mouse full length cDNA for BF-2 and BF-3

Using the corresponding rat cDNA probes, the mouse homologs for BF-2 and BF-3 were isolated from cDNA libraries. The BF-2 cDNA was isolated from a new born mouse brain lambda ZAPII library (purchased from Stragene) and the BF-3 cDNA was isolated from a lambda shlox library from mouse 13 day embryos (purchased from Novagen).

A fragment of rat cDNA was labelled with P-32 and used to screen lambda phage DNA transferred to nitrocellulose membranes. Hybridization and washes were performed as described for the isolation of rat BF-1.

Sequences of the protein coding region of BF-2 are shown in FIGS. 10A and 10B (Seq. I.D. No.3). FIG. 11 (Seq.I.D. No.4) shows a partial sequence of BF-3.

Properties of BF-2 and BF-3

BF-2 is a transcription factor which is expressed in the diencephalon of the central nervous system. It is also expressed in several other sites outside of the nervous system. BF-3 is expressed in the brain and its expression is limited (not ubiquitously expressed).

Human BF-1, BF-2 and BF-3

Human cDNA corresponding to BF-1, BF-2 and BF-3 can be readily obtained by screening a human brain cDNA library using the probes we used to isolate the mouse cDNA. The sequence similarity between rat and mouse cDNA of greater than 95% for all three of these cDNA, implying that the human sequence will also be highly homologous and readily obtainable by these methods.

References:

Bergquist, H. and B. Kallen (1954). Notes on the early histogenesis and morphogenesis of the central nervous system in vertebrates. J. Comp. Neurol. 100: 627–659.

Chomczynski, P. and N. Sacchi (1987). Single-step method of RNA isolation by acid guanidinium thiocyanate-phenol-chloroform extraction. Anal. Biochem. 162: 156–159.

Costa, R. H., D. R. Grayson and J. E. Darnell Jr (1989). Multiple hepatocyte-specific nuclear factors function in the regulation of the transthyretin and a1-antitrypsin genes. Mol. Cell Biol. 9: 1415–1425.

Costa, R. H., E. Lai and J. E. Darnell Jr (1986). Transcriptional control of the mouse prealbumin (transthyretin) gene: Both promoter sequences and a distinct enhancer are cell specific. Mol. Cell Biol. 6: 4697–4708.

Courey, A. and R. Tjian (1988). Analysis of Sp1 in vivo reveals multiple transcriptional domains, including a novel glutamine-rich activation motif. Cell 55: 887–898.

Davis, C. A. and A. L. Joyner (1988). Expression patterns of the homeo box-containing genes En-1 and En-2 and the proto-oncogene int-1 diverge during mouse development. Genes & Dev. 2: 1736–1744.

Davis, C. A., S. E. Noble-Topham, J. Rossant and A. L. Joyner (1988). Expression of the homeo-box containing gene En-2 delineates a specific region of the developing mouse brain. Genes & Dev. 2: 361–371.

Duboule, D. and P. Dolle (1989). The murine Hox gene network: its structural and functional organization resembles that of the Drosophila homeotic genes. EMBO J. 8: 1497–1505.

Ehrlich, M. E., T. Kurihara and P. Greengard (1990). Rat DARPP-32: Cloning, sequencing and characterization of cDNA. J. Mol. Neurosci. 2: 1–10.

Graham, A., N. Papalopulu and Krumlauf (1989). The murine and Drosophila homeobox gene complexes have common features of organization and expression. Cell 57: 367–378.

He, X. and M. G. Rosenfeld (1991). Mechanisms of complex transcriptional regulation: implications for brain development. Neuron 7: 183–196.

He, X., M. Treacy, D. Simmons, et al. (1989). Expression of a large family of POU-domain regulatory genes in mammalian brain development. Nature 340: 35–42.

Hunt, P., M. Gulisano, M. Cook, et al. (1991). A distinct Hox code for the branchial region of the vertebrate head. Nature 353: 861–864.

Jurgens, G. and D. Weigel (1988). Terminal versus segmental development in the Drosophila embryo: the role of the homeotic gene fork head. Roux's Arch. Dev. Biol. 197: 345–354.

Kandel, E., J. H. Schwartz and T. M. Jessell (1991). Principles of Neural Science. New York, Elsevier.

Kessel, M. and P. Gruss (1990). Murine developmental control genes. Science 249: 374–379.

Kozak, M. (1986). Point mutations define a sequence flanking the AUG initiator codon that modulates translation by eukaryotic ribosomes. Cell 44: 283–292.

Kuo, C. F., K. E. Paulson and J. E. Darnell Jr (1988). Positional and developmental regulation of glutamine synthetase expression in mouse liver. Mol. Cell Biol. 8: 4966–4971.

Kuo, C. J., P. B. Conley, L. Chen, et al. (1992). A transcriptional hierarchy involved in mammalian cell-type specification. Nature 355: 457–461.

Lai, E., V. R. Prezioso, E. Smith, et al. (1990). HNF-3A, A hepatocyte-enriched transcription factor of novel structure is regulated transcriptionally. Genes & Dev. 4: 1427–1436.

Lai, E., V. R. Prezioso, W. Tao, W. S. Chen and J. E. Darnell Jr. (1991). Hepatocyte nuclear factor 3a belongs to a gene family in mammals that is homologous to the Drosophila homeotic gene fork head. Genes & Dev. 5: 416–427.

Li, C., C. Lai, D. S. Sigman and R. B. Gaynor (1991). Cloning of a cellular factor, interleukin binding factor, that binds to NFAT-like motifs in the human immunodeficiency virus long terminal repeat. Proc. Natl. Acad. Sci. USA 88: 7739–7743.

Lui, J. K., C. M. DiPersio and K. S. Zaret (1991). Extracellular signals that regulate liver transcription factors during hepatic differentiation in vivo. Mol. Cell Biol. 11: 773–784.

Mangold, O. (1933). Uber die induktions fahigkeit der verschiederen Bezirke der Neurule von Vrodelen. Naturwissenschafter 21: 761–766.

McKay, R. D. G. (1989). The origins of cellular diversity in the mammalian central nervous system. Cell 58: 815–821.

Mermod, N., E. O'Neill, T. Kelly and R. Tjian (1989). The proline-rich transcriptional activator of CTF-NF-1, is distinct from the replication and DNA binding domain. Cell 58: 741–753.

Mori, K., S. C. Fujita, Y. Watanabe, K. Obata and O. Hayaishi (1987). Telencephalon-specific antigen identified by monoclonal antibody. Proc. Natl. Acad. Sci. USA 84: 3921–3925.

Murphy, P., D. R. Davidson and R. E. Hill (1989). Segment-specific expression of a homeobox-containing gene in the mouse hindbrain. Nature 341: 156–159.

Placzek, M., M. Tessier-Lavigne, T. Yamada, T. Jessell and J. Dodd (1990). Mesodermal control of neural cell identity: floor plate induction by the notochord. Science 250: 985–987.

Porteus, M., A. Bulfone, R. Ciaranello and J. Rubenstein (1991). Isolation and characterization of a novel cDNA clone encoding a homeodomain that is developmentally regulated in the ventral forebrain. Neuron 7: 221–229.

Price, M., M. Lemaistre, M. Pischetola, R. DiLauro and D. Duboule (1991). A mouse gene related to Distal-less shows a restricted expression in the developing forebrain. Nature 351: 748–751.

Puissant, C. and L. Houdebine (1990). An improvement of the single-step method of RNA isolation by acid guanidinium thiocyanate-phenol-chloroform extraction. BioTechniques 8: 148–149.

Rosenberg, A. H., B. N. Lade, D. Chui, et al. (1987). Vectors for selective expression of cloned cDNAs by T7 RNA polymerase. Gene 56: 125–135.

Rugh, R. (1968). The mouse: its reproduction and development. New York, Oxford University Press.

Smith, D. B. and K. S. Johnson (1988). Single-step purification of polypeptides expressed in *E. coli* as fusions with glutathione S-transferase. Gene 67: 31–40.

Spemann, H. (1938). Embryonic development and induction. New haven, Yale Univ. Press.

Studier, F. W. and B. A. Moffatt (1986). Use of bacteriophage T7 RNA polymerase to direct selective high-level expression of cloned genes. J. Mol. Biol. 189: 113–130.

Weigel, D. and H. Jackle (1990). Fork head: A new eukaryotic DNA binding motif? Cell 63: 455–456.

Weigel, D., G. Jurgens, F. Kuttner, E. Seifert and H. Jackle (1989). The homeotic gene fork head encodes a nuclear protein and is expressed in the terminal regions of the Drosophila embryo. Cell 57: 645–658.

Wilkinson, D. G., S. Bhatt, P. Chavrier, R. Bravo and P. Charnay (1989). Segment-specific expression of a zinc-finger gene in the developing nervous system of the mouse. Nature 337: 461–464.

Wilkinson, D. C., S. Bhatt, M. Cook, E. Boncinelli and R. Krumlauf (1989). Segmental expression of Hox-2 homeobox-containing genes in the developing mouse hindbrain. Nature 341: 405–409.

Yamada, T., M. Placzek, H. Tanaka, J. Dodd and T. M. Jessell (1991). Control of cell pattern in the developing nervous system: polarizing activity of the floor plate and notochord. Cell 64: 635–647.

What is claimed is:

1. An isolated, animal-derived nucleic encoding Brain Factor-2.
2. The nucleic acid of claim 1, which is an RNA molecule.
3. The nucleic acid of claim 1, which is a DNA molecule.
4. The DNA molecule of claim 3, having Seq. ID No. 3.
5. A plasmid comprising the DNA of claim 3.
6. Plasmid pBSKS-BF-2 (ATCC Accession No. 75460).
7. An isolated, animal-derived nucleic acid encoding Brain Factor-3.
8. The nucleic acid of claim 7, which is an RNA molecule.
9. The nucleic acid of claim 7, which is a DNA molecule.
10. The DNA molecule of claim 9, having Seq. ID No. 4.
11. A plasmid comprising the DNA of claim 9.
12. Plasmid BF-3 (ATCC Accession No. 75461).

* * * * *